United States Patent
Krishnamurthy et al.

(10) Patent No.: US 10,463,624 B2
(45) Date of Patent: Nov. 5, 2019

(54) CONTROLLED RELEASE FORMULATIONS

(71) Applicant: RHODES PHARMACEUTICALS L.P., Coventry, RI (US)

(72) Inventors: Thinnayam N. Krishnamurthy, Scarborough (CA); Andrew Darke, Newmarket (CA)

(73) Assignee: RHODES PHARMACEUTICALS L.P., Coventry, RI (US)

( * ) Notice: Subject to any disclaimer, the term of this patent is extended or adjusted under 35 U.S.C. 154(b) by 0 days.

(21) Appl. No.: 15/714,542

(22) Filed: Sep. 25, 2017

(65) Prior Publication Data
US 2018/0008544 A1  Jan. 11, 2018

Related U.S. Application Data

(60) Division of application No. 15/343,377, filed on Nov. 4, 2016, now Pat. No. 9,949,931, which is a division of application No. 14/718,814, filed on May 21, 2015, now Pat. No. 9,801,823, which is a continuation of application No. 14/049,677, filed on Oct. 9, 2013, now Pat. No. 9,066,869, which is a continuation of application No. 12/283,431, filed on Sep. 11, 2008, now Pat. No. 8,580,310, which is a continuation of application No. 11/879,646, filed on Jul. 17, 2007, now Pat. No. 7,438,930, which is a continuation of application No. 10/156,622, filed on May 28, 2002, now Pat. No. 7,247,318, which is a continuation of application No. 09/465,159, filed on Dec. 16, 1999, now Pat. No. 6,419,960.

(60) Provisional application No. 60/112,617, filed on Dec. 17, 1998.

(51) Int. Cl.
| | |
|---|---|
| A61K 9/14 | (2006.01) |
| A61K 9/16 | (2006.01) |
| A61K 9/24 | (2006.01) |
| A61K 9/50 | (2006.01) |
| A61K 9/20 | (2006.01) |
| A61K 31/4458 | (2006.01) |
| A61K 9/00 | (2006.01) |
| A61K 9/28 | (2006.01) |

(52) U.S. Cl.
CPC ............ *A61K 9/209* (2013.01); *A61K 9/0053* (2013.01); *A61K 9/167* (2013.01); *A61K 9/2081* (2013.01); *A61K 9/2086* (2013.01); *A61K 9/2846* (2013.01); *A61K 9/2893* (2013.01); *A61K 9/5026* (2013.01); *A61K 9/5047* (2013.01); *A61K 9/5073* (2013.01); *A61K 9/5078* (2013.01); *A61K 9/5084* (2013.01); *A61K 9/5089* (2013.01); *A61K 31/4458* (2013.01)

(58) Field of Classification Search
None
See application file for complete search history.

(56) References Cited

U.S. PATENT DOCUMENTS

| | | | |
|---|---|---|---|
| 4,256,108 A | 3/1981 | Theewes | |
| 4,880,830 A | 11/1989 | Rhodes | |
| 4,946,685 A | 8/1990 | Edgren et al. | |
| 5,011,694 A | 4/1991 | Nuernberg et al. | |
| 5,133,974 A | 7/1992 | Paradissis et al. | |
| 5,202,128 A | 4/1993 | Morella et al. | |
| 5,273,760 A | 12/1993 | Oshlack | A61K 9/2866 424/461 |
| 5,286,493 A | 2/1994 | Oshlack et al. | |
| 5,310,558 A | 5/1994 | Pozzi et al. | |
| 5,326,570 A | 7/1994 | Rudnic et al. | |
| 5,356,467 A | 10/1994 | Oshlack et al. | |
| 5,395,626 A | 5/1995 | Kotwal et al. | |
| 5,580,578 A | 12/1996 | Oshlack et al. | |
| 5,639,476 A | 6/1997 | Oshlack | A61K 9/5078 424/468 |
| 5,643,602 A | 7/1997 | Ulmius | |
| 5,658,590 A | 8/1997 | Heiligenstein et al. | |
| 5,773,031 A | 6/1998 | Shah et al. | |
| 5,773,478 A | 6/1998 | Richards et al. | |
| 5,785,994 A | 7/1998 | Wong et al. | |
| 5,837,284 A | 11/1998 | Mehta | A61K 9/1676 424/458 |
| 5,874,090 A | 2/1999 | Baker et al. | |
| 5,885,616 A | 3/1999 | Hsiao | A61K 9/5078 424/461 |
| 5,945,123 A | 8/1999 | Hermelin | |
| 6,077,533 A | 6/2000 | Oshlack et al. | |

(Continued)

FOREIGN PATENT DOCUMENTS

| | | |
|---|---|---|
| CA | 1297368 | 3/1992 |
| EP | 024 8 548 | 9/1987 |

(Continued)

OTHER PUBLICATIONS

Quinn et al., Single-Dose Pharmacokinetics of Multilayer-Release Methylphenidate and Immediate-Release Methylphenidate in Children with Attention-Deficit/ Hyperactivity Disorder, published on Mar. 29, 2007.

(Continued)

*Primary Examiner* — Susan T Tran

(74) *Attorney, Agent, or Firm* — Davidson, Davidson & Kappel, LLC

(57) ABSTRACT

The invention is directed to oral modified/controlled release drug formulations which provide a rapid initial onset of effect and a prolonged duration of effect. Preferably, the peak concentration is lower than that provided by the reference standard for immediate release formulations of the drug, and the duration of effect falls rapidly at the end of the dosing interval.

32 Claims, 8 Drawing Sheets

(56) References Cited

U.S. PATENT DOCUMENTS

| | | | |
|---|---|---|---|
| 6,093,420 | A | 7/2000 | Balchwal |
| 6,143,322 | A | 11/2000 | Sackler |
| 6,214,379 | B1 | 4/2001 | Hermelin |
| 6,255,325 | B1 | 7/2001 | Dariani et al. |
| 6,372,254 | B1 | 4/2002 | Ting et al. |
| 6,419,960 | B1 | 7/2002 | Krishnamurthy et al. |
| 6,673,367 | B1 | 1/2004 | Goldenheim et al. |
| 6,730,325 | B2 | 5/2004 | Devane ............. A61K 9/5084 424/451 |
| 7,083,808 | B2 | 8/2006 | Goldenheim et al. |
| 7,195,778 | B2 | 3/2007 | Fleshner-Barak et al. |
| 7,247,318 | B2 | 7/2007 | Krishnamurthy et al. |
| 7,438,930 | B2 | 10/2008 | Krishnamurthy et al. |
| 2001/0012847 | A1 | 8/2001 | Lam et al. |
| 2010/0151020 | A1 | 6/2010 | Rosenberger et al. |

FOREIGN PATENT DOCUMENTS

| | | |
|---|---|---|
| EP | 0239361 | 9/1987 |
| EP | 0250374 A1 | 12/1987 |
| EP | 0325086 A2 | 7/1989 |
| EP | 0519870 | 12/1992 |
| EP | 0631781 | 1/1995 |
| JP | S55-149211 | 11/1980 |
| JP | S63-115812 | 5/1988 |
| JP | H01-165518 | 6/1989 |
| JP | H02-91028 | 3/1990 |
| JP | 2000-516610 | 12/2000 |
| WO | WO9221333 | 12/1992 |
| WO | WO 97/03673 | 2/1997 |
| WO | WO9703671 | 2/1997 |
| WO | WO9703672 | 2/1997 |
| WO | WO9703673 | 2/1997 |
| WO | WO 98/06380 | 2/1998 |
| WO | WO 98/14168 | 4/1998 |
| WO | WO9814168 | 4/1998 |
| WO | WO 98/18454 | 5/1998 |
| WO | 9823263 | 6/1998 |
| WO | WO 98/48782 | 11/1998 |
| WO | WO 99/08662 | 2/1999 |
| WO | 9962496 | 12/1999 |
| WO | 0025752 | 5/2000 |
| WO | WO 00/35450 | 6/2000 |

OTHER PUBLICATIONS

Dissolution Results of Formulation 1 from Quinn et al., Single-Dose Pharmacokinetics of Multilayer-Release Methylphenidate and Immediate-Release Methylphenidate in Children with Attention-Deficit/Hyperactivity Disorder, published on Mar. 29, 2007.

Product Monograph Biphentin, prepared on Mar. 8, 2006, and revised on Jul. 27, 2007.

Vitiello et al., Methylphenidate Dosage for Children with ADHD Over time Under Controlled Conditions: Lessons From the MTA, J. Am. Acad. Child Adolesc. Psychiatry, 40:2, Feb. 2001.

Swanson et al., The use of a laboratory school protocol to evaluate concepts about efficacy and side effects of new formulations of stimulant medications, Journal of Attention Disorders, vol. 6 Supplement Jan. 2002 , (2002).

McGinity, James W. Aqueous Polymeric Coatings for Pharmaceutical Dosage Forms, Second Edition, pp. 124-125, 272-273, 280-285.

Database HCAPLUS on STN, American Chemical Society, AN 1997:686114, Erramousepe et al., "Effect on Dissolution from Halving Methlyphenidate Extended-Release Tablets," abstract, Ann. Pharmacother., 1997, 31(10), 1123-1126.

English Translation of the Office Action issued in connection with corresponding Japanese application No. 2012-095985 dated Oct. 7, 2014.

The Notice of Opposition filed on Feb. 19, 2009, in connection with European Patent EP 1 140 088.

Office Action issued in connection with European Application No. 08 156 397.5 dated Jan. 23, 2015.

Office Action issued in connection with Japanese Application No. 2012-095985 dated Jun. 30, 2015.

Remington: The Science and Practice of Pharmacy, p. 1592 (1980).

K. Patrick et al., The Absorption of Sustained-Release Methylphenidate Formulations Compared to Immediate-Release Formulation, Biopharmaceutics & Drug Disposition, 10: 165-171, 1989.

P. De Haan & C.F. Lerk, Oral Controlled Release Dosage Forms. A Review, 6 Pharmaceutish Weekblad Scientific Ed., 57-67, 1984.

B. Birmaher, et al., Sustained Release Methylphenidate: Pharmacokinetic Studies in ADDH Males, American Academy of Child and Adolescent Psychiatry, 768-772, 1989.

W.E. Pelham, Jr. et al., Relative Efficacy of Long-Acting Stimulants on Children with Attention Deficit-Hyperactivity Disorder: A Comparison of Standard Methylphenidate, Sustained-Release Methylphenidate, Sustained Release Dextroamphetamine, and Pemoline, Pediatrics, vol. 86, No. 2, 1990.

Corrigan et al., The Biopharmacuetic Drug Classification and Drugs Administered in Extended Release (ER) Formulations, In Vitro-in Vivo Correlations, 111-128, 1997.

CONTROLLED RELEASE FORMULATIONS

This application is a divisional of U.S. application Ser. No. 15/343,377, filed on Nov. 4, 2016, which is a divisional of U.S. application Ser. No. 14/718,814, filed May 21, 2015, which is a continuation of U.S. application Ser. No. 14/049,677, filed Oct. 9, 2013, now U.S. Pat. No. 9,066,869, which is a continuation of U.S. application Ser. No. 12/283,431, filed Sep. 11, 2008, now U.S. Pat. No. 8,580,310, which is a continuation of U.S. application Ser. No. 11/879,646, filed on Jul. 17, 2007, now U.S. Pat. No. 7,438,930; which is a continuation of U.S. application Ser. No. 10/156,622, filed May 28, 2002, now U.S. Pat. No. 7,247,318, which is a continuation of U.S. application Ser. No. 09/465,159, filed Dec. 16, 1999, now U.S. Pat. No. 6,419,960, which claims priority to U.S. Provisional Application No. 60/112,617, filed Dec. 17, 1998, the disclosures of which are hereby incorporated by reference in their entireties.

BACKGROUND OF THE INVENTION

Sustained release dosage forms are central in the search for improved therapy, both through improved patient compliance and decreased incidences of adverse drug reactions. It is the intent of all sustained release formulations to provide a longer period of pharmacologic action after administration than is ordinarily obtained after administration of immediate-release dosage forms. Sustained release compositions may be used to delay absorption of a medicament until it has reached certain portions of the alimentary tract, and maintain a desired concentration of said medicament in the blood stream for a longer duration than would occur if conventional rapid release dosage forms are administered. Such longer periods of response provide for many therapeutic benefits that are not achieved with corresponding short acting, immediate release preparations. Thus, therapy may be continued without interrupting the sleep of the patient, which is of special importance, for example, when treating a patient for moderate to severe pain (e.g., a post-surgery patient, a cancer patient, etc.), or for those patients who experience migraine headaches on awakening, as well as for the debilitated patient for whom sleep is essential. A further general advantage of longer acting drug preparations is improved patient compliance resulting from the avoidance of missed doses through patient forgetfulness.

Unless conventional rapid acting drug therapy is carefully administered at frequent intervals to maintain effective steady state blood levels of the drug, peaks and valleys in the blood level of the active drug occurs because of the rapid absorption, systemic excretion of the compound and through metabolic inactivation, thereby producing special problems in maintenance therapy of the patient. In view of this, it is considered a goal of many skilled in the art that a controlled release dosage form will ideally provide therapeutic concentration of the drug in blood that is maintained throughout the dosing interval with a reduction in the peak/trough concentration ratio. Central to the development process are the many variables that influence the in vivo release and subsequent absorption of the active ingredients from the gastrointestinal tract.

It is known in the pharmaceutical art to prepare compositions which provide for sustained release of pharmacologically active substances contained in the compositions after oral administration to humans and animals. Sustained release formulations known in the art include specially coated pellets, coated tablets and capsules, and ion exchange resins, wherein the slow release of the active medicament is brought about through selective breakdown of the coating of the preparation or through compounding with a special matrix to affect the release of a drug. Some sustained release formulations provide for related sequential release of a single dose of an active compound at predetermined periods after administration.

Sustained release dosage forms are central in the search for improved therapy, both through improved patient compliance and decreased incidences of adverse drug reactions. Ideally, a controlled release dosage form will provide therapeutic concentration of the drug in blood that is maintained throughout the dosing interval with a reduction in the peak/trough concentration ration. Central to the development process are the many variables that influence the in vivo release and subsequent absorption of the active ingredients from the gastrointestinal tract.

Controlled release formulations known in the art include specially coated beads or pellets, coated tablets and ion exchange resins, wherein the slow release of the active drug is brought about through selective breakdown of the coating of the preparation or through formulation with a special matrix to affect the release of the drug. Some controlled release formulations provide for sequential release of a single dosage of an active medicament at predetermined periods after administration.

While controlled and/or sustained release compositions have constituted a definite advance in the art, improvements in these compositions have been sought, particularly for preparations available for conditions such as Attention Deficit Hyperactivity Disorder (ADHD), diabetes etc.

Attention Deficit Disorders are the most common psychiatric disorders in children (Campbell et al. 1992) with reported rates ranging from 4% to 9% (Aman et al. 1983). Attention Deficit Disorder (ADD) is characterized by inattention and impulsivity and may be present with hyperactivity (ADHD) (Shaywitz et al. 1984). Other characteristics may include aggressiveness, stealing, lying, truancy, setting fires, running away, explosiveness, cognitive and learning problems as well as poor social skills (Campbell et al. 1992). It is four to five times more frequent in boys than girls (Campbell et al. 1992).

Stimulant medication, such as amphetamines, have been shown to be the most effective agents in the treatment of children with disorders of activity modulation and attention regulation and result in significant improvement in 70 to 80 percent of affected children (Shaywitz et al. 1984). Positive effects of stimulants have been documented in a variety of areas including behavioral, social, perceptual performance, motor activity, impulse control, attention regulation and cognitive performance (Barkley 1977, Kavale 1983, Offenbacher et al. 1983, Rosenthalet al 1978).

Methylphenidate {dl-threo-methyl-2-phenyl-2-(2-piperidyl) acetate} is the psychostimulant used most frequently in the treatment of hyperactivity and attention deficit disorder. It appears to have a higher incidence of positive effects and a lower incidence of adverse effects than other psychostimulants. The efficacy of methylphenidate ("MPH") in improving attention and behavioral symptoms has been supported by many studies.

Immediate release methylphenidate preparations, because of their short half-life, require frequent administration at short intervals to ensure adequate treatment throughout a child's school day. The rapid onset and offset of immediate release methylphenidate preparations means that a medicated child with attention deficit disorder will be maximally affected only for relatively brief periods during the day. Due to its short half-life, MPH is usually given twice per day, usually once after breakfast and once during the school day, an event that some children and some school personnel apparently avoid, resulting in poor compliance with prescribed regimens (Brown et al., 1985; Firestone 1982). Compliance is a major problem for children who require a midday or midafternoon dose as many schools prohibit children from taking medications during the school day and others often insist that all medications be given by a nurse. Poor compliance in taking medication may explain, in part, the variable and conflicting results reported in many studies of the effect of medication on improving the behavior of hyperactive children. These limitations of immediate release methylphenidate led to interest in products with longer effective periods of action. These limitations of immediate release methylphenidate preparations led to interest in products with longer effective periods of action.

A sustained release form of methylphenidate (Ritalin® SR) is commercially available. As a result of many clinical trials, various opinion leaders in treatment of attention deficit hyperactivity disorder have made the following comments regarding Ritalin® SR (sustained release methylphenidate) produced by Ciba-Geigy: (i) Ritalin® SR does not have a sufficiently early onset of effect to allow for behavioral management in the early morning; (ii) Ritalin® SR does not have the beneficial late effects that would be produced by a lunch time dose of immediate release methylphenidate, thus defeating the purpose of using an SR formulation; (iii) The effects of Ritalin® SR are inconsistent or erratic over the course of the day.

There is a need in the art to develop drug formulations which provide a rapid onset, a prolonged action, followed by rapid offset of effect in order to overcome the deficiencies of the current state of the art.

OBJECTS AND SUMMARY OF THE INVENTION

It is an object of the present invention to provide new oral dosage formulations of methylphenidate or similarly acting drugs which results in improved patient compliance.

It is an object of the present invention to provide new oral dosage formulations which represent improvements over currently available preparations available for conditions such as Attention Deficit Hyperactivity Disorder (ADHD).

It is an object of the present invention to provide new oral dosage formulations of methylphenidate or similarly acting drugs which ensure adequate treatment throughout a child's school day.

It is an object of the present invention to provide new oral dosage formulations which allow a child with attention deficit disorder to be maximally treated throughout the daytime, while being administered only once, i.e., in the morning.

It is a further object of the present invention to provide new controlled/modified release oral dosage formulations which provide a rapid onset and rapid offset with an extended release of active medicaments incorporated therein.

It is yet another object of the present invention to provide new controlled/modified release oral dosage formulations which are useful in all types of pharmaceutically active ingredients and which can extend the time of release of all such ingredients.

It is yet another object of the present invention to provide an oral controlled release formulation which combines both a rapid onset and sustained plasma concentrations throughout the day, followed by a rapid drop-off of plasma concentrations of drug to below minimum effective concentrations.

It is yet another object of the present invention to provide a "multi-layer release" (MLR) technology which is useful for all types of pharmaceutically active ingredients and which can extend the duration of action for a desired length of time.

To address the above-mentioned deficiencies as well as other goals, the present invention is directed in part to a controlled release product which is intended to combined both a rapid onset and sustained plasma concentrations throughout the day. Significantly, the formulations of the present invention provide a rapid onset, a prolonged action, followed by rapid offset of effect, i.e., a "square wave" profile.

The invention is directed in part to controlled/modified release formulations based on a multi-layered release ("MLR") technology. The drug product can be in a tablet or a multiparticulate formulation contained within an oral gelatin capsule.

In the case of beads, encapsulated in a capsule, each bead contains a series of layers with different characteristics—an outer immediate release layer, a release delaying layer (enteric coat), a controlled release layer over an immediate release layer. The MLR formulation is designed such that upon oral administration, the formulation provides a rapid dissolution and absorption of the outer layer of the formulation which contains a portion of the drug in immediate release form, thereby resulting in a rapid rise of the drug to therapeutic plasma levels. This is followed by a period of no absorption (due to an enteric coating), followed thereafter by a controlled release of the drug from the formulation to maintain plasma levels. After absorption of the drug from an immediate release core, plasma levels then rapidly decrease. By virtue of the release of the drug from the MLR formulation, the plasma level of the drug, when plotted on a time/concentration curve, takes the appearance of a "square wave".

In certain further preferred embodiments, the formulation provides a time to maximum plasma concentration at about 0.5 to about 4 hours after oral administration and provides effective blood levels for at least about 6 hours after administration.

In certain further preferred embodiments, the formulation exhibits a "plateau" in the blood plasma curve which lasts from about 2 hours to about 6 hours. Other embodiments exhibit a "plateau" which lasts from about 6 hours to about 12 hours. The "plateau" is characterized by a stabilized plasma concentration, wherein the plasma level at the end of the measured interval does not differ by more than 20%, preferably by no more than 10% of the plasma concentration at the beginning of the measured interval.

In certain further preferred embodiments, the formulation exhibits a bimodal release of active agent from the dosage form. Bimodal release of the active agent is characterized by the active agent being release from the dosage form by more than one distinct release rate. In some embodiments, the release rates can be separated by a no-release or a substantially no-release interval, although this is not always necessary.

In certain further preferred embodiments, the formulation exhibits a biphasic absorption of the active agent. Biphasic absorption of the active agent is characterized by the active agent being absorbed through a natural barrier (e.g. the mucosal lining of the gastro-intestinal tract) by more than one distinct absorption rate. In some embodiments, the absorption rates can be separated by a no-absorption or a substantially no-absorption interval, although this is not always necessary. A formulation can exhibit both biphasic absorption and bimodal release of the active agent, with the biphasic absorption being a function of the bimodal release rate. However, biphasic absorption is not always attributed to release rate and can occur in a formulation not exhibiting bimodal release.

In other preferred embodiments the formulation exhibits bimodal release and/or biphasic absorption to provide a "plateau" in the blood plasma curve which lasts from about 2 hours to about 6 hours. Other embodiments exhibit bimodal release and/or biphasic absorption to provide a "plateau" which lasts from about 6 hours to about 12 hours. Other embodiments maintain effective plasma levels of the active agent for about 16 to about 18 hours after administration of the dosage form.

In certain preferred embodiments, an acrylic resin is utilized to provide the controlled slow release of therapeutically active ingredients over a predetermined or a specified period of time, the acrylic resin thereby comprising a significant part of the "base composition". Base compositions prepared from such acrylic resins provide sustained release of therapeutically active ingredients over a period of time from five hours and for as much as 24 hours after administration, generally oral administration, in humans or animals.

In other embodiments of the invention, the formulations of the invention are composed of:
(i) a mixture of immediate release particles (e.g., beads) and enteric coated immediate release particles (e.g., beads); (ii) a mixture of immediate release particles (e.g., beads) and enteric coated controlled release particles (e.g., beads) or (iii) a mixture of immediate release particles (e.g., beads) and controlled release particles (e.g., beads). In each such instance, the mixture of particles possessing different release properties are blended together and filled into hard gelatin capsules.

In certain preferred embodiments, the controlled/modified release drug formulations of the invention consist of a plurality of beads, each containing an immediate-release component in combination with an enteric coated controlled-release component to produce a delay in the absorption process. The drug product is an oral capsule containing beads. Each bead contains a series of layers with different release characteristics—an outer immediate release layer; a release delaying layer; a controlled release layer; and an immediate release core. The final product is a capsule containing multi-layer release (MLR) beads which have both immediate release and controlled release components. It is made up of a controlled release bead which is enteric coated to delay dissolution until after gastric emptying. The enteric coated controlled release bead has an immediate release topcoat to provide an initial rate of absorption of the drug. In certain embodiments, the immediate release component represents 40% of the total dose per bead and the controlled release component represents 60%. This formulation is designed to produce a rapid rise to therapeutic plasma levels after oral administration, due to the rapid dissolution and absorption of the outer layer, followed by a period of reduced absorption and then controlled release of the immediate release core, to maintain therapeutic plasma levels. After absorption of the immediate release core, plasma levels would then decrease according to the elimination kinetics of the drug. The results of a bioavailability study of this formulation indicate a biphasic release profile that is consistent with the pharmaceutical rationale discussed herein.

In other embodiments of the invention, the bead size of the formulations can be adjusted in order to obtain a desired pharmacokinetic profile based on the correlation between gastric emptying and bead size. A smaller bead size exhibits faster gastric emptying as compared to a larger bead size.

Other objects and advantages of the present invention will be apparent from the further reading of the specification and of the appended claims.

The term "pH-dependent" for purposes of the present invention is defined as having characteristics (e.g. dissolution) which vary according to environmental pH (e.g., due to changes in the in-vitro dissolution media, or due to passage of the dosage form through the gastrointestinal tract.

The term "pH-independent" for purposes of the present invention is defined as having characteristics (e.g., dissolution) which are substantially unaffected by pH, in that a difference, at any given time, between an amount of methylphenidate released at one pH and an amount released at any other pH, when measured in-vitro using the USP Paddle Method of U.S. Pharmacopeia XXII (1990) at 100 rpm in 900 ml aqueous buffer, is no greater than 10%.

BRIEF DESCRIPTION OF THE DRAWINGS

The following drawings are illustrative of embodiments of the invention and are not meant to limit the scope of the invention as encompassed by the claims.

DETAILED DESCRIPTION

Figure 1:
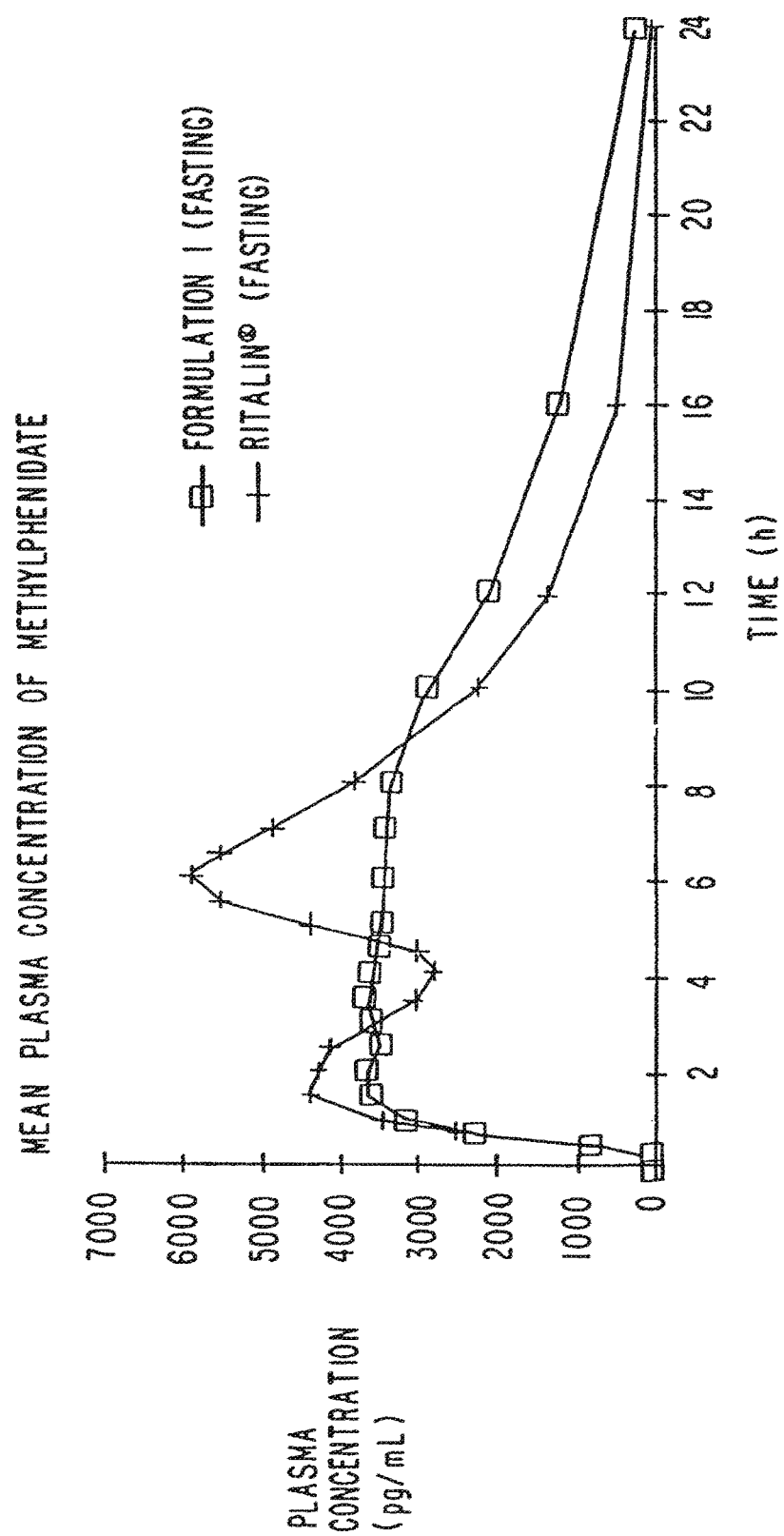
FIG. 1 is a graphical comparison of the mean plasma concentration of methylphenidate when test subjects are treated with Formulation 1 and Ritalin® as a function of time when given under fasting conditions.

The drug used in the formulations of the invention may be selected from a wide variety of pharmaceutically active drugs such as diabetes drugs, attention deficit hyperactivity controlled drugs, analgesics, anti-obesity preparations, anti-inflammatories, antihistamines, antitussives, decongestants, antinausea agents, narcotics, bronchodilators, cardiovasculars, central nervous system (CNS) drugs, nicotine replacement therapy, nitrates, sleeping aids/sedatives, vitamins, etc.

The controlled/modified release preparations of the present invention may be used in conjunction with any multiparticulate system, such as granules, spheroids, beads, pellets, ion-exchange resin beads, and other multiparticulate systems in order to obtain a desired sustained-release of the therapeutically active agent. Beads, granules, spheroids, or pellets, etc., prepared in accordance with the present invention can be presented in a capsule or in any other suitable unit dosage form. An amount of the multiparticulates effective to provide the desired dose of drug over time may be placed in a capsule, may be contained in a packet and sprinkled onto food, or may be incorporated in any other suitable oral solid form, such as a tablet. On the other hand, the present invention can be in the form of a matrix tablet. With respect to all such optional formulations, it is desired that the formulation be prepared such that an initial immediate release of drug provides an early onset of effect, which onset is analogous to an immediate release formulation, and that the formulation further provide a sustained release component which maintains therapeutically effective levels of the drug in the plasma for the desired amount of time, followed by a relatively rapid drop-off in blood plasma levels relative to typical sustained release formulations. Viewed as an in vivo time/concentration plot, the plasma level of the drug from the formulations of the present invention have the appearance of a "square wave". The immediate release component preferably represents from about 30% to about 40% of the total dose and the controlled release component preferably represents from about 60% to about 70% of the total dose of methylphenidate contained in the formulations of the present invention. In certain preferred embodiments, including the MLR embodiments of the invention, the immediate release component represents about 40% of the total dose and the controlled release component represents about 60% of the total dose of methylphenidate contained in the formulation.

In the case of methylphenidate, it is desired that the onset of action occurs from about 0.5 to about 4 hours, and preferably from about 0.5 to about 2 hours after the oral dosage form is administered, and it is further desired that the dosage form no longer provides effective plasma levels of methylphenidate from about 8 to about 12, more preferably from about 8 to about 10 hours, after oral administration of the dose. In this manner, the dose of methylphenidate can be administered to a child in the morning before school begins, provides the desired effect at the start of the school day, with the pharmacologic action of the drug not waning until after the school day ends, and preferably before dinner so that the drug does not have the side effect of acting as an appetite suppressant.

The formulations of the present invention are designed to produce a rapid rise to therapeutic plasma levels after oral administration, due to the rapid dissolution and absorption of the outer layer, followed by a period of reduced absorption and then controlled release of the immediate release core, to maintain therapeutic plasma levels. After absorption of the immediate release core, plasma levels would then decrease according to the elimination kinetics of the drug.

It is generally recognized that the mere presence of an active substance in the gastrointestinal fluids does not, by itself, insure bioavailability. Bioavailability, in a more meaningful sense, is the degree, or amount, to which a drug substance is absorbed into the systemic circulation in order to be available to a target tissue site. To be absorbed, an active drug substance must be in a solution. The time required for a given proportion of an active drug substance contained in a dosage unit to enter into solution in appropriate physiological fluids is known as the dissolution time. The dissolution time for an active substance from a dosage unit is determined as the proportion of the amount of active drug substance released from the dosage unit over a specified time by a test method conducted under standardized conditions. The physiological fluids of the gastrointestinal tract are the media for determining dissolution time. The present state of the art dissolution time for pharmaceutical compositions, and these test procedures are described in official compendia world wide.

Although there are many diverse factors which influence the dissolution of a drug substance from its carrier, the dissolution time determined for a pharmacologically active substance from a specific composition is relatively constant and reproducible. Among the different factors affecting the dissolution time are the surface area of the drug substance presented to the dissolution solvent medium, the pH of the solution, the solubility of the substance in the specific solvent medium, and the driving forces of the saturation concentration of dissolved materials in the solvent medium. Thus, the dissolution concentration of an active drug substance is dynamically modified in this steady state as components are removed from the dissolution medium through absorption across the tissue site. Under physiological conditions, the saturation level of the dissolved materials is replenished from the dosage form reserve to maintain a relatively uniform and constant dissolution concentration in the solvent medium, providing for a steady state absorption.

The transport across a tissue absorption site in the gastrointestinal tract is influenced by the Donnan osmotic equilibrium forces on both sides of the membrane, since the direction of the driving force is the difference between the concentrations of active substance on either side of the membrane, i.e. the amount dissolved in the gastrointestinal fluids and the amount present in the blood. Since the blood levels are constantly being modified by dilution, circulatory changes, tissue storage, metabolic conversion and systemic excretion, the flow of active materials is directed from the gastrointestinal tract into the blood stream.

Notwithstanding the diverse factors influencing both dissolution and absorption of a drug substance, in many cases an important correlation can be established between the in vitro dissolution time determined for a dosage form and the in vivo bioavailability. This correlation is so firmly established in the art that dissolution time has become generally descriptive of bioavailability potential for many classes of active components contained in a particular dosage form. In view of this relationship, the dissolution time determined for a composition is one of the important fundamental characteristics for consideration when evaluating whether a controlled release formulation should be tested in vivo.

With the above in mind, the in-vitro dissolution of the drug at various time points for formulations in accordance with the present invention is provided below:

| Time (hours) | % Drug Dissolved |
|---|---|
| 0.25 | 0-45% |
| 1 | 5-50% |
| 4 | 40-90% |

| Time (hours) | % Drug Dissolved |
| --- | --- |
| 8 | NLT 60% |
| 12 | NLT 80% |

In certain preferred embodiments of the present invention, the in-vitro dissolution of the drug at various time points for formulations in accordance with the present invention is provided below:

| Time (hours) | % Drug Dissolved |
| --- | --- |
| 0.25 | 0-45% |
| 1 | 10-50% |
| 4 | 30-80% |
| 8 | NLT 65% |
| 12 | NLT 80% |

Sustained Release Coatings

In certain preferred embodiments, the drug is incorporated into or onto a substrate and a sustained release coating is applied thereto. For example, the drug may be contained within or on a substrate as follows: (i) incorporated into matrix spheroids (e.g., together with a pharmaceutically acceptable spheronizing agent such as microcrystalline cellulose), (ii) coated onto inert pharmaceutically acceptable beads (e.g., nonpareil beads); (iii) incorporated into a normal release tablet core; or (iv) incorporated into a tablet core which comprises a matrix including a sustained release carrier material. Thereafter, a sustained release coating is applied onto substrates such as those mentioned in (i)-(iv) above. The dosage forms of the present invention may optionally be coated with one or more materials suitable for the regulation of release or for the protection of the formulation. In one embodiment, coatings are provided to permit either pH-dependent or pH-independent release, e.g., when exposed to gastrointestinal fluid. A pH-dependent coating serves to release the drug in desired areas of the gastrointestinal (GI) tract, e.g., the stomach or small intestine. When a pH-independent coating is desired, the coating is designed to achieve optimal release regardless of pH-changes in the environmental fluid, e.g., the GI tract. It is also possible to formulate compositions which release a portion of the dose in one desired area of the GI tract, e.g., the stomach, and release the remainder of the dose in another area of the GI tract, e.g., the small intestine.

Formulations according to the invention that utilize pH-dependent coatings to obtain formulations may also impart a repeat-action effect whereby unprotected drug is coated over the enteric coat and is released in the stomach, while the remainder, being protected by the enteric coating, is released further down the gastrointestinal tract. Coatings which are pH-dependent may be used in accordance with the present invention include shellac, cellulose acetate phthalate (CAP), polyvinyl acetate phthalate (PVAP), hydroxypropylmethylcellulose phthalate, and methacrylic acid ester copolymers, zein, and the like.

In certain preferred embodiments, the substrate (e.g., tablet core bead, matrix particle) comprising the drug is coated with a hydrophobic material selected from (i) an alkylcellulose; (ii) an acrylic polymer; or (iii) mixtures thereof. The coating may be applied in the form of an organic or aqueous solution or dispersion. The coating may be applied to obtain a weight gain from about 2 to about 25% of the substrate in order to obtain a desired sustained release profile. Such formulations are described, e.g., in detail in U.S. Pat. Nos. 5,273,760 and 5,286,493, assigned to the Assignee of the present invention and hereby incorporated by reference. The particles are preferably film coated with a material that permits release of the drug so as to achieve, in combination with the other stated properties, a desired in-vitro release rate and in-vivo plasma levels. The sustained release coating formulations of the present invention should be capable of producing a strong, continuous film that is smooth and elegant, capable of supporting pigments and other coating additives, non-toxic, inert, and tack-free.

Other examples of sustained release formulations and coatings which may be used in accordance with the present invention include Assignee's U.S. Pat. Nos. 5,324,351; 5,356,467, and 5,472,712, hereby incorporated by reference in their entirety.

Alkylcellulose Polymers

Cellulosic materials and polymers, including alkylcelluloses, provide hydrophobic materials well suited for coating the beads according to the invention. Simply by way of example, one preferred alkylcellulosic polymer is ethylcellulose, although the artisan will appreciate that other cellulose and/or alkylcellulose polymers may be readily employed, singly or in any combination, as all or part of a hydrophobic coating according to the invention.

One commercially available aqueous dispersion of ethylcellulose is Aquacoat® (FMC Corp., Philadelphia, Pa., U.S.A.). Aquacoat® is prepared by dissolving the ethylcellulose in a water-immiscible organic solvent and then emulsifying the same in water in the presence of a surfactant and a stabilizer. After homogenization to generate submicron droplets, the organic solvent is evaporated under vacuum to form a pseudolatex. The plasticizer is not incorporated in the pseudolatex during the manufacturing phase. Thus, prior to using the same as a coating, it is necessary to intimately mix the Aquacoat® with a suitable plasticizer prior to use.

Another aqueous dispersion of ethylcellulose is commercially available as Surelease® (Colorcon, Inc., West Point, Pa., U.S.A.). This product is prepared by incorporating plasticizer into the dispersion during the manufacturing process. A hot melt of a polymer, plasticizer (dibutyl sebacate), and stabilizer (oleic acid) is prepared as a homogeneous mixture, which is then diluted with an alkaline solution to obtain an aqueous dispersion which can be applied directly onto substrates.

Acrylic Polymers

The hydrophobic material comprising the controlled release coating may comprise a pharmaceutically acceptable acrylic polymer, including but not limited to acrylic acid and methacrylic acid copolymers, methyl methacrylate copolymers, ethoxyethyl methacrylates, cyanoethyl methacrylate, poly(acrylic acid), poly(methacrylic acid), methacrylic acid alkylamide copolymer, poly(methyl methacrylate), polymethacrylate, poly(methyl methacrylate) copolymer, polyacrylamide, aminoalkyl methacrylate copolymer, poly (methacrylic acid anhydride), and glycidyl methacrylate copolymers.

In certain preferred embodiments, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

In order to obtain a desirable dissolution profile, it may be necessary to incorporate two or more ammonio methacrylate copolymers having differing physical properties, such as different molar ratios of the quaternary ammonium groups to the neutral (meth)acrylic esters.

Certain methacrylic acid ester-type polymers are useful for preparing pH-dependent coatings which may be used in accordance with the present invention. For example, there are a family of copolymers synthesized from diethylaminoethyl methacrylate and other neutral methacrylic esters, also known as methacrylic acid copolymer or polymeric methacrylates, commercially available as Eudragit® from Röhm Tech, Inc. There are several different types of Eudragit®. For example, Eudragit® E is an example of a methacrylic acid copolymer which swells and dissolves in acidic media. Eudragit® L is a methacrylic acid copolymer which does not swell at about pH<5.7 and is soluble at about pH>6. Eudragit® S does not swell at about pH<6.5 and is soluble at about pH>7. Eudragit® RL and Eudragit® RS are water swellable, and the amount of water absorbed by these polymers is pH-dependent, however, dosage forms coated with Eudragit® RL and RS are pH-independent.

In certain preferred embodiments, the acrylic coating comprises a mixture of two acrylic resin lacquers commercially available from Rohm Pharma under the Tradenames Eudragit® RL30D and Eudragit® RS30D, respectively. Eudragit® RL30D and Eudragit® RS30D are copolymers of acrylic and methacrylic esters with a low content of quaternary ammonium groups, the molar ratio of ammonium groups to the remaining neutral (meth)acrylic esters being 1:20 in Eudragit® RL30D and 1:40 in Eudragit® RS30D. The mean molecular weight is about 150,000. The code designations RL (high permeability) and RS (low permeability) refer to the permeability properties of these agents. Eudragit® RL/RS mixtures are insoluble in water and in digestive fluids. However, coatings formed from the same are swellable and permeable in aqueous solutions and digestive fluids.

The Eudragit® RL/RS dispersions of the present invention may be mixed together in any desired ratio in order to ultimately obtain a sustained release formulation having a desirable dissolution profile. Desirable sustained release formulations may be obtained, for instance, from a retardant coating derived from 100% Eudragit® RL, 50% Eudragit® RL and 50% Eudragit® RS, and 10% Eudragit® RL: 90% Eudragit® RS. Of course, one skilled in the art will recognize that other acrylic polymers may also be used, such as, for example, Eudragit® L.

Plasticizers

In embodiments of the present invention where the coating comprises an aqueous dispersion of a hydrophobic material such as an alkylcellulose or an acrylic polymer, the inclusion of an effective amount of a plasticizer in the aqueous dispersion of hydrophobic material will further improve the physical properties of the sustained release coating. For example, because ethylcellulose has a relatively high glass transition temperature and does not form flexible films under normal coating conditions, it is preferable to incorporate a plasticizer into an ethylcellulose coating containing sustained release coating before using the same as a coating material. Generally, the amount of plasticizer included in a coating solution is based on the concentration of the film-former, e.g., most often from about 1 to about 50 percent by weight of the film-former. Concentration of the plasticizer, however, can only be properly determined after careful experimentation with the particular coating solution and method of application.

Examples of suitable plasticizers for ethylcellulose include water insoluble plasticizers such as dibutyl sebacate, diethyl phthalate, triethyl citrate, tributyl citrate, and triacetin, although it is possible that other water-insoluble plasticizers (such as acetylated monoglycerides, phthalate esters, castor oil, etc.) may be used. Triethyl citrate is an especially preferred plasticizer for the aqueous dispersions of ethyl cellulose of the present invention.

Examples of suitable plasticizers for the acrylic polymers of the present invention include, but are not limited to citric acid esters such as triethyl citrate NE XVI, tributyl citrate, dibutyl phthalate, and possibly 1,2-propylene glycol. Other plasticizers which have proved to be suitable for enhancing the elasticity of the films formed from acrylic films such as Eudragit® RL/RS lacquer solutions include polyethylene glycols, propylene glycol, diethyl phthalate, castor oil, and triacetin. Triethyl citrate is an especially preferred plasticizer for the aqueous dispersions of ethyl cellulose of the present invention.

It has further been found that the addition of a small amount of talc reduces the tendency of the aqueous dispersion to stick during processing, and acts as a polishing agent.

When the aqueous dispersion of hydrophobic material is used to coat a substrate including the drug, for example, inert pharmaceutical beads such as nu pariel 18/20 beads, a plurality of the resultant stabilized solid controlled release beads may thereafter be placed in a gelatin capsule in an amount sufficient to provide an effective controlled release dose when ingested and contacted by an environmental fluid, e.g., gastric fluid or dissolution media. Alternatively, the substrate may be a tablet core coated with the sustained release coating, and optionally a further film-forming agent or colorant, such as Opadry®.

In formulations where an aqueous dispersion of an hydrophobic polymer such as an alkylcellulose is applied to the substrate, it is preferred that the coated substrate is cured at a temperature above the glass transition temperature of the plasticized polymer and at a relative humidity above ambient conditions, until an endpoint is reached at which the coated formulation attains a dissolution profile which is substantially unaffected by exposure to storage conditions, e.g., of elevated temperature and/or humidity. Generally, in such formulations the curing time is about 24 hours or more, and the curing conditions may be, for example, about 60° C. and 85% relative humidity. Detailed information concerning the stabilization of such formulations is set forth in U.S. Pat. Nos. 5,273,760; 5,681,585; and 5,472,712; all of which are hereby incorporated by reference in their entireties.

In formulations where an aqueous dispersion of an acrylic polymer is applied to the substrate, it is preferred that the coated substrate is cured at a temperature above the glass transition temperature of the plasticized polymer until an endpoint is reached at which the coated formulation attains a dissolution profile which is substantially unaffected by exposure to storage conditions, e.g., of elevated temperature and/or humidity. Generally, the curing time is about 24 hours or more, and the curing temperature may be, for example, about 45° C. Detailed information concerning the stabilization of such formulations is set forth in U.S. Pat. Nos. 5,286,493; 5,580,578; and 5,639,476; all of which are hereby incorporated by reference in their entireties.

The sustained release profile of the coated formulations of the invention can be altered, for example, by varying the amount of overcoating with the aqueous dispersion of hydrophobic material, altering the manner in which the plasticizer is added to the aqueous dispersion of hydrophobic material, by varying the amount of plasticizer relative to hydrophobic material, by the inclusion of additional ingredients or excipients, by altering the method of manufacture, etc. The dissolution profile of the ultimate product may also be modified, for example, by increasing or decreasing the thickness of the retardant coating.

Spheroids or beads coated with a therapeutically active agent are prepared, e.g., by dissolving the therapeutically active agent in water and then spraying the solution onto a substrate, for example, nu pariel 18/20 beads, using a Wuster insert. Optionally, additional ingredients are also added prior to coating the beads in order to assist the binding of the drug to the beads, and/or to color the solution, etc. For example, a product which includes hydroxypropylmethylcellulose, etc. with or without colorant (e.g., Opadry®, commercially available from Colorcon, Inc.) may be added to the solution and the solution mixed (e.g., for about 1 hour) prior to application of the same onto the beads. The resultant coated substrate, in this example beads, may then be optionally overcoated with a barrier agent, to separate the therapeutically active agent from the hydrophobic controlled release coating. An example of a suitable barrier agent is one which comprises hydroxypropylmethylcellulose. However, any film-former known in the art may be used. It is preferred that the barrier agent does not affect the dissolution rate of the final product.

The beads may then be overcoated with an aqueous dispersion of the hydrophobic material. The aqueous dispersion of hydrophobic material preferably further includes an effective amount of plasticizer, e.g. triethyl citrate. Pre-formulated aqueous dispersions of ethylcellulose, such as Aquacoat® or Surelease®, may be used. If Surelease is used, it is not necessary to separately add a plasticizer. Alternatively, pre-formulated aqueous dispersions of acrylic polymers such as Eudragit can be used.

The coating solutions of the present invention preferably contain, in addition to the film-former, plasticizer, and solvent system (i.e., water), a colorant to provide elegance and product distinction. Color may be added to the solution of the therapeutically active agent instead, or in addition to the aqueous dispersion of hydrophobic material. For example, color be added to Aquacoat via the use of alcohol or propylene glycol based color dispersions, milled aluminum lakes and opacifiers such as titanium dioxide by adding color with shear to water soluble polymer solution and then using low shear to the plasticized Aquacoat. Alternatively, any suitable method of providing color to the formulations of the present invention may be used. Suitable ingredients for providing color to the formulation when an aqueous dispersion of an acrylic polymer is used include titanium dioxide and color pigments, such as iron oxide pigments. The incorporation of pigments, may, however, increase the retard effect of the coating.

The plasticized aqueous dispersion of hydrophobic material may be applied onto the substrate comprising the therapeutically active agent by spraying using any suitable spray equipment known in the art. In a preferred method, a Wurster fluidized-bed system is used in which an air jet, injected from underneath, fluidizes the bore material and effects drying while the acrylic polymer coating is sprayed on. A sufficient amount of the aqueous dispersion of hydrophobic material to obtain a predetermined sustained release of the therapeutically active agent (i.e., drug) when the coated substrate is exposed to aqueous solutions, e.g. gastric fluid, is preferably applied, taking into account the physical characteristics of the therapeutically active agent, the manner of incorporation of the plasticizer, etc. After coating with the hydrophobic material, a further overcoat of a film-former, such as Opadry, is optionally applied to the beads. This overcoat is provided, if at all, in order to substantially reduce agglomeration of the beads.

The release of the drug from the sustained release formulation of the present invention can be further influenced, i.e., adjusted to a desired rate, by the addition of one or more release-modifying agents, or by providing one or more passageways through the coating. The ratio of hydrophobic material to water soluble material is determined by, among other factors, the release rate required and the solubility characteristics of the materials selected.

The release-modifying agents which function as pore-formers may be organic or inorganic, and include materials that can be dissolved, extracted or leached from the coating in the environment of use. The pore-formers may comprise one or more hydrophilic materials such as hydroxypropylmethylcellulose.

The sustained release coatings of the present invention can also include erosion-promoting agents such as starch and gums.

The sustained release coatings of the present invention can also include materials useful for making microporous lamina in the environment of use, such as polycarbonates comprised of linear polyesters of carbonic acid in which carbonate groups reoccur in the polymer chain.

The release-modifying agent may also comprise a semipermeable polymer.

In certain preferred embodiments, the release-modifying agent is selected from hydroxypropylmethylcellulose, lactose, metal stearates, and mixtures of any of the foregoing.

The sustained release coatings of the present invention may also include an exit means comprising at least one passageway, orifice, or the like. The passageway may be formed by such methods as those disclosed in U.S. Pat. Nos. 3,845,770; 3,916,889; 4,063,064; and 4,088,864 (all of which are hereby incorporated by reference). The passageway can have any shape such as round, triangular, square, elliptical, irregular, etc.

The substrate of the present invention may be prepared by a spheronizing agent together with the active agent ingredient that can be spheronized to form spheroids. Microcrystalline cellulose is preferred. A suitable microcrystalline cellulose is, for example, the material sold as Avicel PH 101 (Trade Mark, FMC Corporation). In such embodiments, in addition to the active ingredients and spheronizing agent, the spheroids may also contain a binder. Suitable binders, such as low viscosity, water soluble polymers, will be well known to those skilled in the pharmaceutical art. However, water soluble hydroxy lower alkyl cellulose, such as hydroxypropylcellulose, are preferred. Additionally (or alternatively) the spheroids may contain a water insoluble polymer, especially an acrylic polymer, an acrylic copolymer, such as a methacrylic acid-ethyl acrylate copolymer or ethyl cellulose. In such embodiments, the sustained-release coating will generally include a water insoluble material such as (a) a wax, either alone or in admixture with a fatty alcohol; or (b) shellac or zein.

In a particular preferred embodiment of the invention, the controlled/modified release methylphenidate formulation is prepared as a multilayered release (MLR) formulation comprising coated inert beads. A summary of one method of manufacturing such a formulation is outlined as follows. First, immediate release (IR) drug-coated beads are prepared by spraying a solution of methylphenidate in water over sugar beads in a fluid bed dryer with a drug load of about 8%. The spray process is carried out in a fluid bed dryer, equipped with a Wurster column. A clear overcoat of HPMC is applied using an Opadry® material (e.g., Opadry® Clear (Formula No: YS-1-7006)), to a weight gain of about 1%. Next, a controlled release coating is applied to the IR beads, which converts the same into controlled release (CR) beads. This is accomplished by spraying a solution of Eudragit® RS 30 D, triethyl citrate (plasticizer) and talc (glidant), onto the IR beads. Next, the coated beads are cured in order to obtain a stabilized release rate of the therapeutically active agent. In preferred embodiments of the present invention where the CR coating utilizes an acrylic resin to control the release of the drug, the CR beads at this stage are subjected to oven curing at a temperature above the Tg of the plasticized acrylic polymer of the required time period, the optimum values of the temperature and time for the particular formulation being determined experimentally. In certain embodiments of the present invention, the stabilized products is obtained via oven curing conducted at a temperature of about 40-50° C. for a time period of about 12 to about 24 hours or longer. An enteric coating is then applied onto the CR beads to convert the same into enteric coated CR (ECCR) beads. This is accomplished by spraying a solution of Eudragit® L 30 D-55 dispersion, triethyl citrate (plasticizer) and talc (glidant) onto the CR beads. Finally, an immediate release coating is applied onto the ECCR beads (referred to as, e.g., an IR Topcoat). This is accomplished by spraying a solution of methylphenidate in water over EC CR beads.

Results of initial studies show that this formulation is stable under room temperature (25° C., 60% RH) and accelerated conditions (40° C., 75% RH).

In certain preferred embodiments of the present invention, an effective amount of the drug in immediate release form is included in the drug formulation. The immediate release form of the drug is included in an amount which is effective to shorten the time to maximum concentration of the drug in the blood (e.g., plasma), such that time to $T_{max}$ is shortened to a time of, e.g., from about 0.5 to about 2 hours. By including an amount of immediate release drug in the formulation, the time to onset of action is significantly reduced, and is the same or earlier than that of the reference standard immediate release treatment (e.g., Ritalin IR). In such embodiments, an effective amount of the drug in immediate release form may be coated onto the substrates (e.g., multiparticulates or tablets) of the present invention. For example, where the extended release of the drug from the formulation is due to a controlled release coating, the immediate release layer can be overcoated on top of the controlled release coating. On the other hand, the immediate release layer may be coated onto the surface of substrates wherein the drug is incorporated in a controlled release matrix. Where a plurality of the sustained release substrates comprising an effective unit dose of the drug (e.g., multiparticulate systems including pellets, spheres, beads and the like) are incorporated into a hard gelatin capsule, the immediate release portion of the drug dose may be incorporated into the gelatin capsule via inclusion of the sufficient amount of immediate release drug as a powder or granulate within the capsule. Alternatively, the gelatin capsule itself may be coated with an immediate release layer of the drug. One skilled in the art would recognize still other alternative manners of incorporating the immediate release drug portion into the unit dose. Such alternatives are deemed to be encompassed by the appended claims.

DETAILED DESCRIPTION OF THE PREFERRED EMBODIMENTS

The following examples illustrate various aspects of the present invention. They are not to be construed to limit the claims in any manner whatsoever.

EXAMPLE 1

Methylphenidate HCl Immediate Release Beads

TABLE 1

| Ingredients | % |
|---|---|
| Methylphenidate hydrochloride | 15.0 |
| Sugar bead 14/18 | 80.0 |
| Opadry ® clear YS-1-7006 | 5.0 |
| Water | q.s. |
| Total | 100.0 |

1. Charge Niro-Aeromatic Strea 1 Fluid Bed Wurster Coater with 14/18 mesh Nupareil® PG (sugar spheres NF).
2. Coat the beads at 60° C. by spraying a solution of methylphenidate hydrochloride (12% w/w) and Opadry clear (4% w/w) in water.
3. Once the coating is completed, allow the beads to dry at 60° C. for 2 or 3 minutes.
4. Cool the beads in a shallow pan at room temperature.
5. Break agglomerates, if any.
6. Sift the beads through Tyler 10 mesh sieve (1.77 mm opening) and then through Tyler 20 mesh sieve (850 micrometer opening) to remove fines.
7. Apply top coat to beads by spraying a solution of coloured Opadry clear solution (4% w/w) to a theoretical weight gain of 1% w/w.

After the completion of the overcoat, the beads are then filled into hard gelatin capsules at a strength of 20 mg.

Dissolution-testing was conducted on the bead filled IR capsules using USP Apparatus 1 (basket method) in 500 mL of simulated gastric juice without enzyme, 100 rpm at 37° C. The results are as follows:

TABLE 2

| Time (minutes) | % Methylphenidate HCl dissolved |
|---|---|
| 10 | 92.7 |
| 20 | 95.7 |
| 30 | 97.7 |
| 45 | 98.5 |

The dissolution results as set forth in the above table indicate that 98.5% of the methylphenidate hydrochloride was dissolved in 45 minutes.

EXAMPLE 2

Methylphenidate HCl Controlled-release (CR) Beads with Acrylic Polymer Coating

TABLE 3

| Ingredients | % |
| --- | --- |
| Methylphenidate IR beads | 86.20 |
| Eudragit ® RS 30 D | 8.63 |
| Triethyl citrate | 1.72 |
| Talc | 3.45 |
| Water | q.s. |
| Total | 100.0 |

The controlled-release coating is manufactured as follows:

1. The Eudragit® RS 30 D is plasticized with triethyl citrate and talc approximately 30 minutes.
2. A load of the IR beads is charged into a Wurster insert of an Aeromatic Fluid Bed Dryer with 1 mm spray nozzle and the beads are coated to a weight gain of ~8%.
3. Upon completion of the coating, the beads are cured for 24 hours at 40-45° C.

The beads were then filled into hard gelatin capsules at a 20 mg strength.

Dissolution testing was conducted on the bead filled CR capsules using the following USP Apparatus (basket method). The capsules were placed into 500 mL of simulated gastric juice without enzyme, for first 2 hours at 100 rpm and 37° C. and then placed into 500 mL simulated intestinal fluid without enzyme for the remainder of the testing period. The results are as follows:

TABLE 4

| Time (hours) | Methylphenidate HCl dissolved |
| --- | --- |
| 1 | 6.9 |
| 2 | 16.2 |
| 3 | 26.1 |
| 4 | 35.7 |
| 6 | 59.8 |
| 8 | 74.7 |
| 12 | 75.4 |
| 18 | 82.5 |
| 24 | 92.8 |

The dissolution results as set forth in the above table indicate that 92.8% of methylphenidate hydrochloride dissolved in 24 hours.

EXAMPLES 3 & 4

Dependence of Release Rate of Methylphenidate HCl from Controlled-Release (CR) Beads on Amount of Acrylic Polymer Coating By adjusting the amount of Eudragit® RS 30 D applied, the release rate can be adjusted. This effect is illustrated in Examples 3 and 4 below:

TABLE 5

| | % | |
| --- | --- | --- |
| Ingredients | Example 3 | Example 4 |
| Methylphenidate HCl IR Bead | 91.2 | 94.0 |
| Eudragit ® RS 30 D | 5.8 | 3.9 |
| Triethyl citrate | 1.0 | 0.7 |
| Talc | 2.0 | 1.4 |
| Water | — | — |
| Total | 100.0 | 100.0 |

The method of manufacturing the controlled-release beads in Examples 3 and 4 is similar to the method described under Example 2, by varying the proportion of beads and Eudragit® RS 30 D.

The cured beads were filled into hard gelatin capsules at a strength of 20 mg.

The dissolution results, conducted under conditions identical to those found under Example 2, are shown below:

TABLE 6

| | % Methylphenidate HCl dissolved | |
| --- | --- | --- |
| Time (hours) | Example 3 | Example 4 |
| 1 | 18.7 | 49.5 |
| 2 | 35.1 | 73.3 |
| 3 | 49.0 | 81.5 |
| 4 | 60.6 | 85.2 |
| 6 | 75.7 | 90.4 |
| 8 | 77.3 | 90.7 |
| 12 | 82.1 | 92.8 |

The dissolution results as set forth in the above table, indicate that 82.1% and 92.8% respectively of methylphenidate hydrochloride is dissolved in 12 hours. However, the release of drug from Example 4 was significantly faster at time points 1, 2, 3, 4, 6 and 8 hours.

EXAMPLE 5

Enteric Coated (EC) Coated Release (CR) Beads—EC•CR Beads

TABLE 7

| Ingredients | % |
| --- | --- |
| Methylphenidate CR beads | 83.2 |
| Eudragit ® L 30 D55 | 9.9 |
| Triethyl citrate | 2.0 |
| Talc | 49 |
| Water | q.s. |
| Total | 100.0 |

The enteric coating procedure is described below:
1. The Eudragit® L 30 D 55 is plasticized with triethyl citrate and talc approximately 30 minutes.
2. A load of the methylphenidate CR beads is charged into a Wurster insert of an Aeromatic Fluid Bed Dryer with 1 mm spray nozzle and the beads are coated to a weight gain of ~9%.
3. Upon completion of the coating, the beads are cured for 18 hours at 40° C.
4. The cured beads are then sieved through Tyler 10 mesh (1.7 mm opening) and Tyler 20 mesh (850 micrometer opening) sieves to remove any fines.

The beads were then filled into hard gelatin capsules at a 20 mg strength.

Dissolution testing was conducted on the bead filled CR filled capsules using USP Apparatus 1 (basket method) 500 mL at 100 rpm and 37° C. using SGF without enzyme for the first 2 hours and SIF without enzyme for the rest of the testing period. Results are shown below:

TABLE 8

| Time (hours) | % Methylphenidate HCl dissolved | | |
|---|---|---|---|
| | Lot 1 | Lot 2 | Lot 3 |
| 1 | 0.4 | 1.0 | 2.0 |
| 2 | 2.2 | 5.4 | 7.4 |
| 3 | 18.8 | 27.8 | 61.3 |
| 4 | 36.7 | 48.3 | 87.0 |
| 6 | 59.5 | 75.5 | 98.8 |
| 8 | 76.9 | 90.1 | 100.0 |
| 12 | 82.3 | 99.6 | — |

The dissolution results as set forth in the above table indicate that very little drug is dissolved in gastric juice after enteric coating and that the dissolution profile of the CR beads has been modified.

EXAMPLE 6

Formulations for Clinical Trials

Examples 6A, 6B and 6C below set forth the formulations developed and tested in clinical studies.

EXAMPLE 6A: (IR•EC•CR Beads)

Immediate Release (IR) Coating of Enteric Coated Controlled-Release (EC•CR) Methylphenidate Beads The (IR•EC•CR Beads) formulation, hereinafter referred to as Formulation 1, is a capsule containing multi-layer release beads which have both immediate release and controlled release components. It is made up of a controlled release bead which is enteric coated to delay dissolution until after gastric emptying. The enteric coated controlled release bead has an immediate release topcoat to provide an initial rate of absorption equal to or greater than Ritalin® IR immediate release tablets. The immediate release component represent 40% of the total dose per bead and the controlled release component represents 60%.

TABLE 9

| Ingredients | % |
|---|---|
| Enteric coated Controlled Release Methylphenidate HCl beads | 91.4 |
| Methylphenidate hydrochloride USP | 6.5 |
| Opadry ® clear YS-1-7006 | 2.1 |
| Water | q.s. |
| Total | 100.0 |

The application of an immediate release coat on the top of Enteric Coated CR beads is described below:
1. Dissolve methylphenidate HCl USP and Opadry in water with stirring.
2. Load EC•CR beads into a Wurster insert of an Aeromatic Fluid Bed Dryer.
3. Spray the beads with the coating solution using a 1 mm spray nozzle at a temperature of not more than 50° C.
4. Once the coating is completed, cool the beads at room temperature and pass through Tyler sieves 10 and 20 mesh to remove fines.

The beads were then filled into a hard gelatin capsule to a 20 mg strength.

Dissolution testing was conducted on the bead filled capsules of Formulation 1 using USP Apparatus 1 (basket method) 100 rpm, 500 mL at 37° C.—simulated gastric juice without enzyme 1st and 2nd hours; 3rd hour onwards simulated intestinal fluid without enzyme.

The results are as follows:

TABLE 10

| Time (hours) | % Methylphenidate HCl dissolved |
|---|---|
| 5 minutes | 37.0 |
| 10 minutes | 38.0 |
| 15 minutes | 39.0 |
| 30 minutes | 40.0 |
| 60 minutes | 40.0 |
| 2 | 40.1 |
| 3 | 51.4 |
| 4 | 61.0 |
| 6 | 75.6 |
| 8 | 87.0 |
| 12 | 87.5 |

The dissolution results as set forth in the above table indicate a rapid onset on dissolution, followed by prolonged action.

EXAMPLE 6B: (IR+EC•CR Blend)

Combination of Immediate Release Methylphenidate Beads (IR) and Enteric Coated Controlled-Release (EC•CR) Methylphenidate Beads The enteric-coated controlled release beads (EC•CR) beads described in Example 5 may be mixed with the immediate release (IR) beads described in Example 1 in varying proportions and placed in capsules to obtain the final blended dosage form, (IR+EC•CR Blend), hereinafter referred to as Formulation 2. Formulation 2 was designed to provide a faster rate of absorption of the controlled release portion than Formulation 1. The immediate release component represents 35% of the total dose per capsule and the controlled release component represents 65%.

Dissolution testing was performed and the comparative results are shown in Table 11 below.

EXAMPLE 6C: (IR•CR Beads)

Immediate Release (IR Coating of Controlled-Release (CR) Methylphenidate Beads

The IR•CR Beads formulation, hereinafter referred to as Formulation 3, is a capsule containing single beads made up of an immediate release topcoat and a controlled release core, and is designed to provide an intermediate rate of absorption of the controlled release portion between that of the controlled release formulations of Formulations 1 and 2. The immediate release component represents 30% of the total dose per bead and the controlled release component represents 70%.

The immediate release topcoat is applied to CR beads as described in Example 6A for Formulation 1.

The dissolution profiles of Formulations 1-3 and Ritalin® SR, used as a comparator, are shown in Table 11 below. Hours 1 and 2 are in 500 ml of simulated gastric fluid. Simulated intestinal fluid (500 ml) is used from the third hour onwards. The results of the dissolution testing confirmed the anticipated in vitro dissolution profile.

TABLE 11

Comparative Dissolution of Formulations

| Time (Hours) | Ritalin SR | Formulation 1 | Formulation 2 | Formulation 3 |
|---|---|---|---|---|
| 10 min | 21.4 | 38.0 | 32.0 | 28.6 |
| 30 min | 31.4 | 40.0 | 36.7 | 34.0 |
| 1 | 45.7 | 40.0 | 38.2 | 40.5 |
| 2 | 62.3 | 40.1 | 40.4 | 57.6 |
| 3 | 75.8 | 51.4 | 68.1 | 70.6 |
| 4 | 79.5 | 61.0 | 86.4 | 79.5 |
| 6 | 88.0 | 75.6 | 95.4 | 89.6 |
| 8 | 90.7 | 87.0 | 96.2 | 92.7 |
| 12 | 91.3 | 87.5 | 97.0 | 93.1 |

EXAMPLE 7

Four Way Comparison of Single Dose Formulation 1 (Fed and Fasted) with Two Doses of Ritalin IR (Fed and Fasted)

The bioavailability of Methylphenidate MLR capsules was investigated in a four-way blind study which compared the Formulation 1 20 mg single dosage formulation under fed and fasted conditions with two doses (4 hours apart) of Ritalin® IR.

Healthy male volunteers were given a single dose of 20 mg Formulation 1 or two doses of immediate release methylphenidate 10 mg administered four hours apart under both fed and fasting conditions (n=12). "Fed" conditions indicates the test formulation was given to the subjects after they had eaten a high-fat breakfast. Following an overnight fast of at least 10.0 hours, each of the normal, healthy, non-smoking, male subjects were given the following treatments according to Williams design 4 treatment randomization scheme.

Treatment 1: Test Product: methylphenidate controlled-release, Formulation 1, 20 mg capsule, in the morning under fasting conditions.

Treatment 2: Reference Product: methylphenidate immediate-release, Ritalin® (Novartis), 10 mg tablet in the morning and 4 hours later, under fasting conditions.

Treatment 3: Test Product: methylphenidate controlled-release, Formulation 1, 20 mg capsule, administered 5 minutes after a high fat breakfast.

Treatment 4: Reference Product: methylphenidate immediate-release, Ritalin® (Novartis), 10 mg tablet in the morning and 4 hours later, administered 5 minutes after a high fat breakfast.

There was a seven day washout period between the study periods. During each study period, blood samples (1×5 mL each) were taken from each subject within one hour prior to dosing and at 0.250, 0.500, 0.750, 1.00, 1.50, 2.00, 2.50, 3.00, 3.50, 4.00, 4.50, 5.00, 6.00, 7.00, 8.00, 10.0, 12.0, 16.0, 24.0 hours post-dose for the Formulation 1 and at pre-dose, 0.250, 0.500, 0.750, 1.00, 1.50, 2.00, 2.50, 3.00, 3.50, 4.00, 4.50, 5.00, 6.00, 7.00, 8.00, 10.0, 12.0, 16.0, 24.0 hours post-dose for the Ritalin® IR. Plasma was harvested from each blood sample and stored in a −20° C. freezer until assayed for plasma methylphenidate concentration. Assay of plasma methylphenidate concentrations was performed using gas chromatography/mass spectrometry (GC/MS).

The mean plasma concentrations, standard deviations and coefficients of variation are shown as a function of time in Tables 12 and 13, for fasting and fed conditions, respectively.

Figure 2:
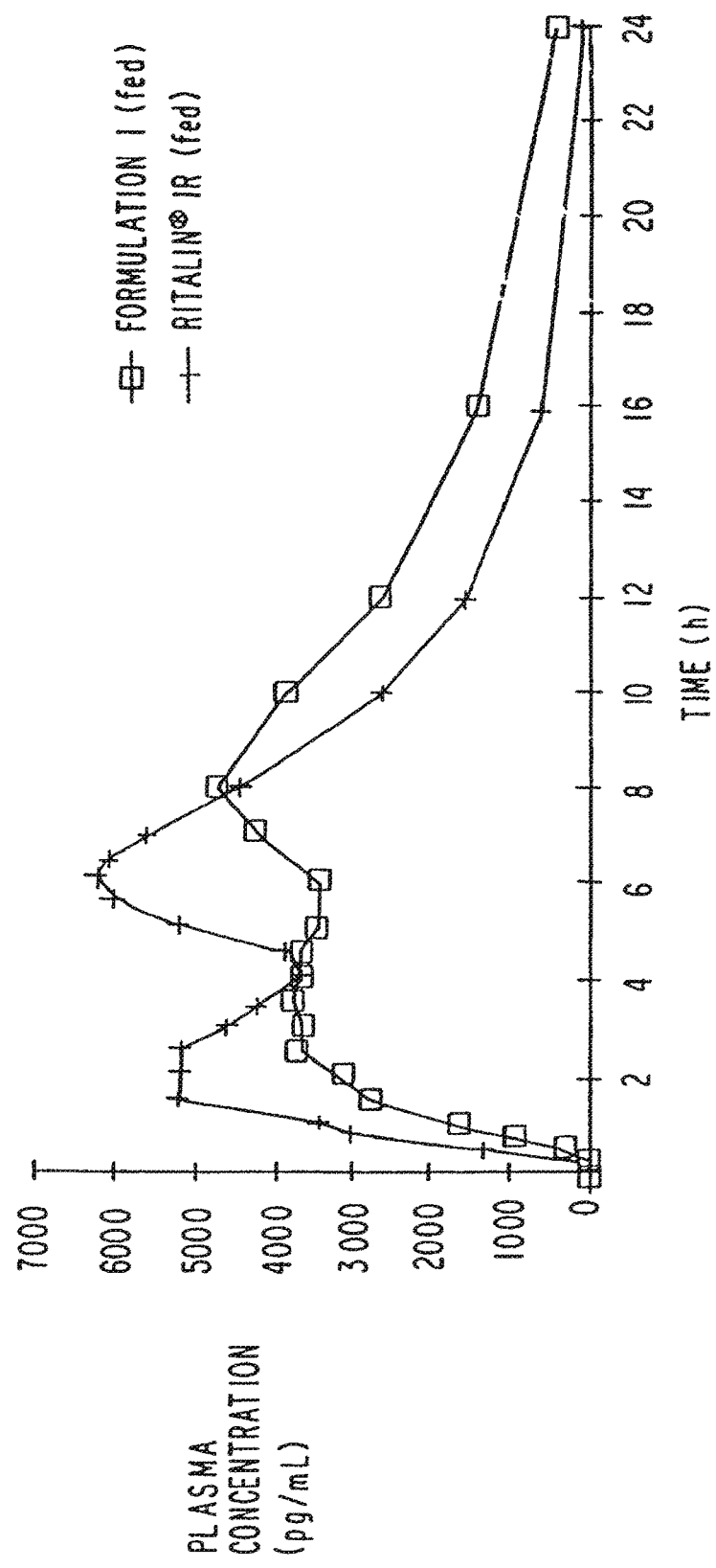
FIG. 2 is a graphical comparison of the mean plasma concentration of methylphenidate when test subjects are treated with Formulation 1 and Ritalin® as a function of time when given under fed conditions.
Figure 3:
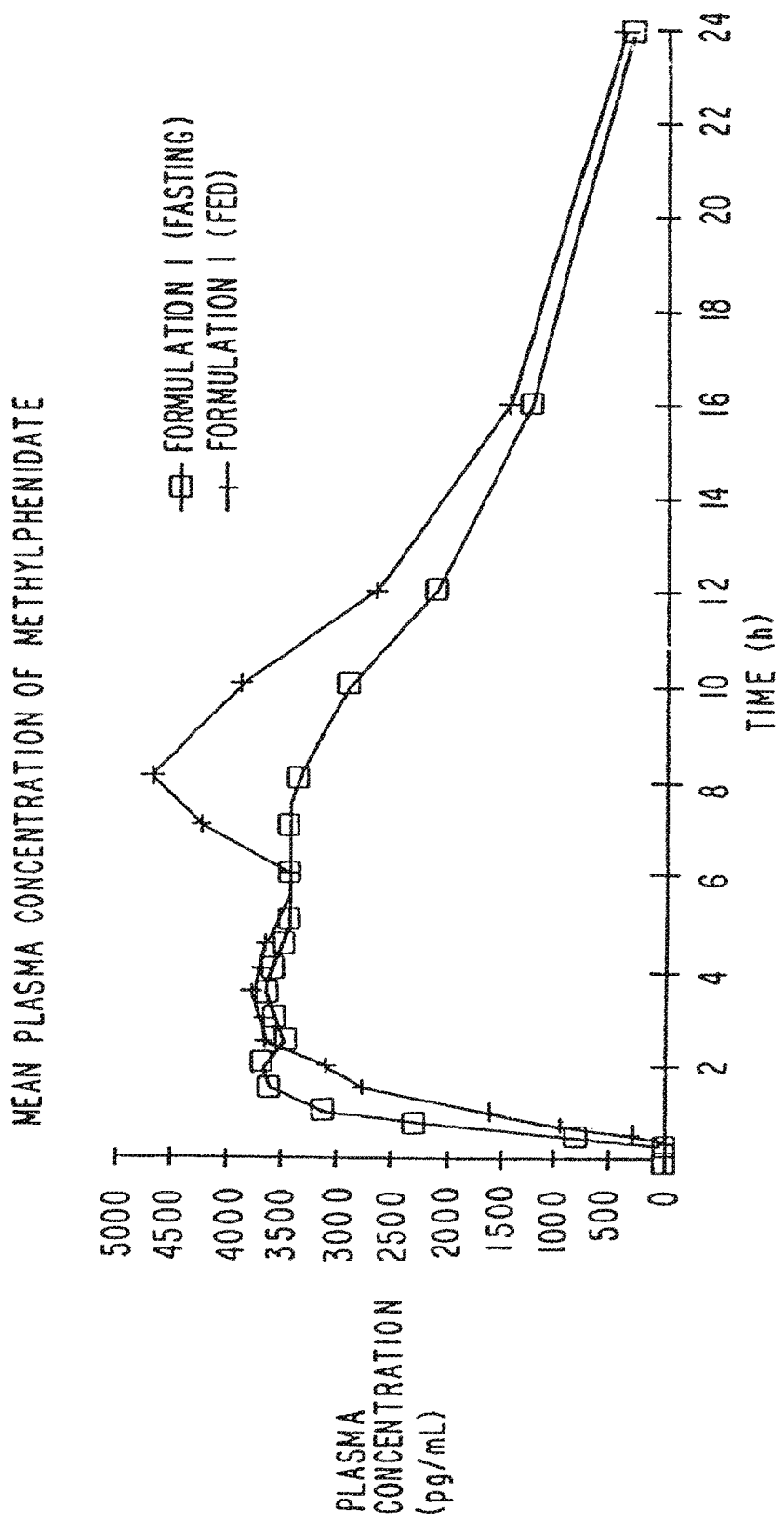
FIG. 3 is a graphical comparison of the mean plasma concentration of methylphenidate when test subjects are treated with Formulation 1 as a function of time when given under fasting and fed conditions.
Figure 4:
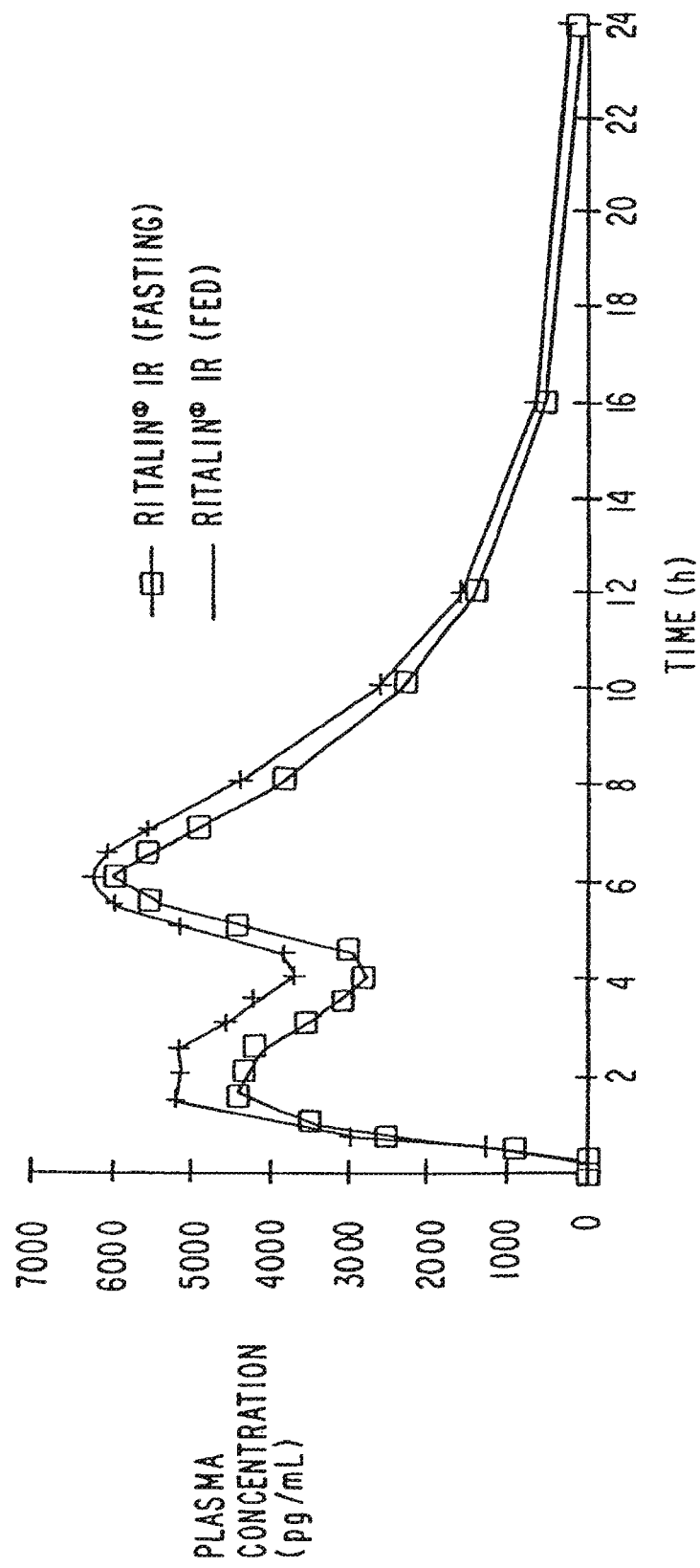
FIG. 4 is a graphical comparison of the mean plasma concentration of methylphenidate when test subjects are treated with Ritalin® as a function of time when given under fasting and fed conditions.

This data is presented graphically in FIGS. 1-4. FIG. 1 presents the mean plasma concentration versus time for Formulation 1 and Ritalin® under fasting conditions. FIG. 2 presents the mean plasma concentration versus time for Formulation 1 and Ritalin® under fed conditions. FIG. 3 presents the mean plasma concentration versus time for Formulation 1 under fed and fasting conditions. FIG. 4 presents the mean plasma concentration versus time for Ritalin® under fed and fasting conditions.

TABLE 12

Mean Plasma Concentrations (pg/mL) of Methylphenidate: Formulation 1 and Ritalin ®IR (fasting)

| Sample Time (h) | Formulation 1 | | | Ritalin | | |
|---|---|---|---|---|---|---|
| | Concentration | SD (±) | CV (%) | Concentration | SD (±) | CV (%) |
| 0.000 | 0.00 | 0.00 | | 0.00 | 0.00 | |
| 0.250 | 0.00 | 0.00 | — | 0.00 | 0.00 | |
| 0.500 | 817.53 | 801.84 | 98.08 | 883.96 | 686.65 | 77.68 |
| 0.750 | 2268.79 | 1128.12 | 49.72 | 2485.74 | 828.38 | 33.33 |
| 1.00 | 3108.79 | 756.66 | 24.34 | 3468.74 | 1172.28 | 33.80 |
| 1.50 | 3597.88 | 740.36 | 20.58 | 4388.04 | 998.86 | 22.76 |
| 2.00 | 3675.60 | 1315.29 | 35.78 | 4289.39 | 1144.40 | 26.68 |
| 2.50 | 3469.81 | 882.62 | 25.44 | 4121.37 | 1014.57 | 24.62 |
| 3.00 | 3573.56 | 1031.61 | 28.87 | 3528.56 | 863.25 | 24.46 |
| 3.50 | 3637.01 | 1008.73 | 27.74 | 3020.93 | 716.36 | 23.71 |
| 4.00 | 3604.03 | 1071.59 | 29.73 | 2747.91 | 698.95 | 25.44 |
| 4.50 | 3494.44 | 1069.13 | 30.60 | 2958.49 | 799.89 | 27.04 |
| 5.00 | 3446.41 | 1069.50 | 31.03 | 4394.22 | 1603.40 | 36.49 |
| 5.50 | — | — | | 5525.84 | 1766.58 | 31.97 |
| 6.00 | 3421.13 | 1166.25 | 34.09 | 5927.06 | 1955.99 | 33.00 |
| 6.50 | | — | — | 5528.41 | 1758.49 | 31.81 |
| 7.00 | 3422.32 | 958.42 | 28.00 | 4860.45 | 1482.24 | 30.30 |
| 8.00 | 3338.59 | 724.49 | 21.70 | 3795.34 | 1500.79 | 39.54 |
| 10.0 | 2858.42 | 612.21 | 21.42 | 2223.48 | 926.11 | 41.65 |
| 12.0 | 2073.97 | 536.08 | 25.85 | 1334.71 | 523.37 | 39.21 |

TABLE 12-continued

Mean Plasma Concentrations (pg/mL) of Methylphenidate:
Formulation 1 and Ritalin ®IR (fasting)

| Sample Time | Formulation 1 | | | Ritalin | | |
|---|---|---|---|---|---|---|
| (h) | Concentration | SD (±) | CV (%) | Concentration | SD (±) | CV (%) |
| 16.0 | 1180.67 | 502.11 | 42.53 | 455.86 | 287.79 | 63.13 |
| 24.0 | 275.87 | 201.51 | 73.04 | 55.10 | 99.99 | 181.46 |

TABLE 13

Mean Plasma Concentrations (pg/mL) of Methylphenidate:
Formulation 1 and Ritalin ® IR (fed)

| Sample Time | Formulation 1 | | | Ritalin | | |
|---|---|---|---|---|---|---|
| (h) | Concentration | SD (±) | CV (%) | Concentration | SD (±) | CV (%) |
| 0.000 | 0.00 | 0.00 | — | 0.00 | 0.00 | |
| 0.250 | 0.00 | 0.00 | — | 53.12 | 133.84 | 251.95 |
| 0.500 | 291.66 | 271.58 | 93.11 | 1256.61 | 1602.66 | 127.54 |
| 0.750 | 910.22 | 653.80 | 71.83 | 2984.60 | 3406.53 | 114.14 |
| 1.00 | 1580.66 | 983.13 | 62.20 | 3400.39 | 2301.87 | 67.69 |
| 1.50 | 2760.68 | 797.24 | 28.88 | 5205.16 | 1882.17 | 36.16 |
| 2.00 | 3098.73 | 874.49 | 28.22 | 5146.55 | 1617.43 | 31.43 |
| 2.50 | 3655.68 | 982.31 | 26.87 | 5157.11 | 1227.99 | 23.81 |
| 3.00 | 3625.88 | 797.35 | 22.00 | 4546.61 | 932.94 | 20.52 |
| 3.50 | 3717.71 | 951.58 | 25.60 | 4184.34 | 1080.71 | 25.83 |
| 4.00 | 3650.63 | 875.97 | 23.99 | 3652.57 | 1023.22 | 28.01 |
| 4.50 | 3627.41 | 835.40 | 23.03 | 3811.27 | 1103.83 | 28.96 |
| 5.00 | 3430.14 | 783.72 | 22.85 | 5158.45 | 1714.53 | 33.24 |
| 5.50 | — | — | — | 5982.98 | 1618.65 | 27.05 |
| 6.00 | 3418.03 | 937.07 | 27.42 | 6228.81 | 1591.64 | 25.55 |
| 6.50 | — | — | — | 6054.32 | 1919.95 | 31.71 |
| 7.00 | 4218.94 | 775.86 | 18.39 | 5538.57 | 1741.02 | 31.43 |
| 8.00 | 4679.67 | 1126.52 | 24.07 | 4350.90 | 1611.95 | 37.05 |
| 10.0 | 3858.58 | 1045.56 | 27.10 | 2577.66 | 896.59 | 34.78 |
| 12.0 | 2610.98 | 902.53 | 34.57 | 1521.52 | 611.54 | 40.19 |
| 16.0 | 1372.86 | 737.71 | 53.74 | 577.90 | 334.26 | 57.84 |
| 24.0 | 334.79 | 306.63 | 91.59 | 94.23 | 144.99 | 153.86 |

EXPERIMENTAL RESULTS

Pharmacokinetic parameters were calculated based on the data from the four-way study. $AUC_{0-t}$ (pg·h/mL), $AUC_{0-inf}$ (pg·h/mL), $AUC_{t/inf}$(%), $C_{max}$ (pg/mL), $T_{max}$ (hours), $T_{1/2\ el}$ (hours), $K_{el}$ (hour$^{-1}$), TLIN (hours) and LQCT (hours) were calculated as described below.

For purposes of the present invention, the following terms are meant to have the following meanings:
Analysis of Pharmacokinetic Data and Statistical Analysis
$AUC_{0-inf}$ Area under the concentration-time curve from time zero to the time of the last non-zero concentration (this corresponds to the area under the concentration-time curve, over the dosing interval of the test formulation for both controlled-release and immediate-release formulations)
$AUC_{0-inf}$ Area under the concentration-time curve from time zero to infinity
C.I. Confidence interval
CV Coefficient of variation
$C_{max}$ Maximum observed concentration
$K_{el}$ Elimination rate constant
LQCT The last quantifable concentration time
SD Standard deviation
TLIN The time point where log-linear elimination begins
$T_{1/2\ el}$ Time for observed $C_{max}$ Sampling Time Time post dose of plasma collection based on parameters to be studied
Scheduled Time The predetermined (clock) time at which the samples are to be taken
Actual time The exact (clock) time at which the sample was taken Time deviations during sampling for drugs with a $T_{max} \leq 4$ hours were treated as follows: between 0 and 6 hours post dose, the sampling time was used in the statistical analysis if the delay between the actual and scheduled time of blood collection was <10%. Above 6 hours post dose, the sampling time was used in the statistical analysis if the delay between the actual and scheduled time of plasma collection was <15%. When sampling times were used when previously described acceptance criteria, the corrected sampling items were used when performing pharmacokinetic parameters calculations. Sampling times are present in concentration tables and graphs of statistical report.

The mean, standard deviation (SD), and coefficient of variation (CV) were calculated for plasma concentrations of methylphenidate for each sampling time and treatment. As well, the mean, SD, and CV were calculated for the $AUC_{0-t}$ (pg·h/mL), $AUC_{0-inf}$(pg·h/mL), $C_{max}$ (pg/mL), $T_{max}$ (hours), $T_{1/2\ el}$ (hours), $K_{el}$ (hour$^{-1}$), TLIN (hours) and LQCT (hours). The calculation of these pharmacokinetic parameters is explained below.

Areas Under the Concentration-Time Curves $AUC_{0-t}$ was calculated using the linear trapezoidal rule.

The $AUC_{0-t}$ was derived where t is the time (t) of the last measurable (non-zero) concentration ($C_t$) for each treatment.

The $AUC_{0-inf}$ was calculated as:

$$AUC_{0-t} + \frac{C_t}{K_{el}}$$

Where $C_t$=the last non-zero concentration for that treatment, $AUC_{0-t}$=the AUC from time zero to the time of the last non-zero concentration for that treatment and $K_{el}$=the elimination rate constant.

Maximum Observed Concentration and Time of Observed Peak Concentration

The maximum observed concentration, $C_{max}$, and the observed time to reach peak concentration, $T_{max}$, was determined for each subject and for each treatment.

Half-Life and Elimination Rate Constant

To calculate the elimination rate constant ($K_{el}$), linear regression analyses were performed on the natural log (Ln) of plasma concentration values (y) versus time (x). Calculations were made between a time point where log-linear elimination phase begins (LQCT) occurred. The $K_{el}$ was taken as the slope multiplied by (−1) and the apparent half-life ($T_{1/2\ el}$) as $0.693/K_{el}$.

TLIN and LQCT

TLIN, the time point where log-linear elimination begins, and LQCT, the last quantifiable concentration time were determined for each subject and for each treatment.

Percent Drug Absorbed Percent drug absorbed was calculated at each sampling time (t) by Modified Wagner-Nelson's method, as implemented in Kinetica software, version 2.0.1 according to the following formula:

$$\frac{C_t + (K_{el} \times AUC_{0-t})}{(K_{el} \times AUC_{0-inf})} \times 100$$

All ANOVAs were performed with the SAS General Linear Models Procedure (GLM). For all analyses, effects were considered statistically significant if the probability associated with 'F' was less than 0.050. Based on the pairwise comparisons of the ln-transformed $AUC_{0-t}$, $AUC_{0-inf}$ and $C_{max}$ data, the relative ratios of the geometric means, calculated according to the formulation "$e^{(X-Y)} \times 100$", as well as the 90% geometric confidence intervals were determined.

The plasma concentration of unchanged methylphenidate following administration of the controlled release formulation Formulation 1 reached the maximum concentration ($C_{max}$) at a mean of 3.27 hours under fasting conditions and 7.29 hours under fed conditions reflecting a biphasic absorption profile. The plasma concentration of unchanged methylphenidate following administration of two doses of the immediate release formulation (Ritalin® IR) reached the maximum concentration ($C_{max}$) at 5.96 hours under fasting conditions and 3.54 hours under fed conditions. When the determination of $C_{max}$ was restricted to the first dose of immediate release methylphenidate, the $T_{max}$ was 1.71 hours under fasting conditions and 1.63 hours under fed conditions.

The complete pharmacokinetic parameters of controlled release methylphenidate 20 mg Formulation 1 and immediate release methylphenidate 10 mg (Ritalin® IR) under fed and fasted conditions are summarized in Tables 14 and 15 below.

TABLE 14

Pharmacokinetic Parameters for Formulation 1

| Parameters | Formulation 1 (fasting) Mean ± SD | CV (%) | Formulation 1 (fed) Mean ± SD | CV (%) |
|---|---|---|---|---|
| $AUC_{0-t}$ (pg · h/mL) | 48493.80 ± 13430.27 | 27.69 | 54686.38 ± 15118.66 | 27.65 |
| $AUC_{0-inf}$ (pg · h/mL) | 51213.86 ± 13260.14 | 26.59 | 57931.47 ± 16762.54 | 28.94 |
| $C_{max}$ (pg/mL) | 4410.25 ± 1188.68 | 26.95 | 4879.37 ± 1027.85 | 21.07 |
| $T_{max}$ (h) | 3.27 ± 2.54 | 77.64 | 7.29 ± 1.29 | 17.65 |
| $K_{el}$ (h$^{-1}$) | 0.1672 ± 0.0339 | 20.25 | 0.1812 ± 0.0392 | 21.65 |
| $T_{1/2\ el}$ (h) | 4.32 ± 0.96 | 22.18 | 4.06 ± 1.25 | 30.91 |

TABLE 15

Pharmacokinetic Parameters for Ritalin ® IR

| Parameters | RITALIN® (fasting) Mean ± SD | CV (%) | RITALIN® (fed) Mean ± SD | CV (%) |
|---|---|---|---|---|
| $AUC_{0-t}$ (pg · h/mL) | 44644.22 ± 13806.82 | 30.93 | 52781.49 ± 15194.94 | 28.79 |
| $AUC_{0-inf}$ (pg · h/mL) | 46466.23 ± 14012.73 | 30.16 | 54783.17 ± 15311.08 | 27.95 |
| $C_{max}$ (pg/mL) | 6536.04 ± 1669.29 | 25.54 | 7571.74 ± 1534.58 | 20.27 |
| $T_{max}$ (h) | 5.96 ± 0.54 | 9.09 | 3.54 ± 2.42 | 68.43 |
| $K_{el}$ (h$^{-1}$) | 0.2481 ± 0.0550 | 22.17 | 0.2449 ± 0.0719 | 29.37 |
| $T_{1/2\ el}$ (h) | 2.93 ± 0.71 | 24.10 | 3.08 ± 0.96 | 31.26 |

The results of the ANOVA and Duncan's Multiple Range Test performed on the ln-transformed $AUC_{0-t}$ data show a statistically significant difference between treatments for this parameter. According to Duncan's Multiple Range Test, the $AUC_{0-t}$ of treatment 1 was significantly different from the $AUC_{0-t}$ of treatments 2 and 3. However, Duncan's Multiple Range Test did not detect statistically significant differences between treatments 3 and 4 for this parameter. The statistical analyses performed on the data are summarized in Table 16 below:

TABLE 16

| $AUC_{0-t}$ (pg · h/mL) | TRT 1 vs. TRT 2 | TRT 3 vs. TRT 4 | TRT 1 vs. TRT 3 |
|---|---|---|---|
| Ratio | 109.90% | 104.08% | 88.65% |
| 90% Geometric C.I. | 102.59% to 117.74% | 97.15% to 111.50% | 82.75% to 94.97% |

The results of the ANOVA and Duncan's Multiple Range Test performed on the ln-transformed $AUC_{0-inf}$ data show a statistically significant difference between treatments for this parameter. According to Duncan's Multiple Range Test, the $AUC_{0-inf}$ of treatment 1 was significantly different from the $AUC_{0-inf}$ of treatments 2 and 3. However, Duncan's Multiple Range Test did not detect statistically significant differences between treatments 3 and 4 for this parameter. The statistical analyses performed on the data are summarized below in Table 17:

TABLE 17

| AUC$_{0-inf}$ (pg · h/mL) | TRT 1 vs. TRT 2 | TRT 3 vs. TRT 4 | TRT 1 vs. TRT 3 |
|---|---|---|---|
| Ratio | 111.65% | 105.86% | 88.85% |
| 90% Geometric C.I. | 104.09% to 119.95% | 98.70% to 113.55% | 82.84% to 95.30% |

The results of the ANOVA and Duncan's Multiple Range Test performed on the ln-transformed $C_{max}$ data show a statistically significant difference between treatments for this parameter. According to Duncan's Multiple Range Test, the $C_{max}$ of treatment 1 was not significantly different from the $C_{max}$ of treatment 3. However, Duncan's Multiple Range Test detected statistically significant differences for $C_{max}$ when comparing treatments 1 and 2 and treatments 3 and 4. The statistical analyses performed on the data are summarized below in Table 18:

TABLE 18

| $C_{max}$ (pg/mL) | TRT 1 vs. TRT 2 | TRT 3 vs. TRT 4 | TRT 1 vs. TRT 3 |
|---|---|---|---|
| Ratio | 67.48% | 64.38% | 89.37% |
| 90% Geometric C.I. | 60.28% to 75.54% | 57.51% to 72.07% | 79.83% to 100.04% |

The ANOVA and Duncan's Multiple Range Test performed on the $T_{max}$ data detected a statistically significant difference between treatments for this parameter. Duncan's Multiple Range Test detected statistically significant differences between treatments 1 and 2, treatments 3 and 4, and treatments 1 and 3 for this parameter.

The ANOVA and Duncan's Multiple Range Test performed on the $T_{1/2\ el}$ data detected a statistically significant difference between treatments for this parameter. Duncan's Multiple Range Test detected no statistically significant differences between treatments 1 and 3 for $T_{1/2\ el}$. However, Duncan's Multiple Range Test detected statistically significant differences between treatments 1 and 2 and treatments 3 and 4 for this parameter.

The results of the ANOVA and Duncan's Multiple Range Test performed on the $K_{el}$ data show a statistically significant difference between treatments for this parameter. Statistically significant differences were detected by Duncan's Multiple Range Test between treatments 1 and 2 and treatments 3 and 4, but not for treatments 1 and 3.

Summary and Analysis

The AUC and $C_{max}$ ratios of controlled release methylphenidate 20 mg Formulation 1 under fed and fasted conditions are summarized in Table 19 below. A comparison of the AUC and $C_{max}$ ratios for immediate release methylphenidate 10 mg (Ritalin® IR) and Formulation 1 under fasting conditions are summarized in Table 20 below. Table 21 shows the comparative ratios for immediate release methylphenidate 10 mg (Ritalin® IR) and Formulation 1 under fed conditions.

Treatment 1 (Formulation 1, Fasting) Versus Treatment 3 (Formulation 1, Fed)

The ANOVAs detected statistically significant differences between treatments for ln-transformed $AUC_{0-t}$, $AUC_{0-inf}$ and $C_{max}$, and untransformed $T_{max}$, $K_{el}$, $T_{1/2\ el}$. Duncan's Multiple Range Test detected statistically significant differences between treatments 1 and 3 for ln-transformed $AUC_{0-t}$ and $AUC_{0-inf}$ and untransformed $T_{max}$. However, Duncan's Multiple Range Test detected no statistically significant differences between treatments for ln-transformed $C_{max}$ and untransformed $K_{el}$ and $T_{1/2\ el}$. All formulation ratios, as well as 90% geometric confidence intervals of the relative mean $AUC_{0-t}$, $AUC_{0-inf}$ and $C_{max}$ of the test product (Formulation 1, fasting) to reference product (Formulation 1, fed) were found to be within 80 to 125%. This is summarized in Table 19 below:

TABLE 19

| Formulation 1 (Fed) vs. Formulation 1 (Fast) | | | |
|---|---|---|---|
| | $AUC_{0-t}$ | $AUC_{0-inf}$ | $C_{max}$ |
| Ratio[1] | 112.80% | 112.54% | 111.90% |
| 90% Geometric C.I.[2] | 105.29%- 120.84% | 104.93%- 120.71% | 99.96%- 125.27% |

[1]Calculated using geometric means according to the formula: $e^{[Formulation\ 1(fed)\ -\ Formulation\ 1\ (fasting)]} \times 100$
[2]90% Geometric Confidence Interval using ln-transformed data Treatment 1 (Formulation 1, Fasting) Versus Treatment 2 (Ritalin®, Fasting)

The ANOVAs detected statistically significant differences between treatments for ln-transformed $AUC_{0-t}$, $AUC_{0-inf}$ and $C_{max}$, and untransformed $T_{max}$, $K_{el}$, $T_{1/2\ el}$. Duncan's Multiple Range Test detected statistically significant differences between treatments 1 and 2 for all parameters. With the exception of $C_{max}$, all formulation ratios as well as 90% geometric confidence intervals of the relative mean $AUC_{0-t}$ and $AUC_{0-inf}$ of the test product (Formulation 1) to reference product (Ritalin) were found to be within the 80 to 125%. This is summarized in Table 20 below:

TABLE 20

| Formulation 1 (Fast) vs Ritalin ® (Fast) | | | |
|---|---|---|---|
| | $AUC_{0-t}$ | $AUC_{0-inf}$ | $C_{max}$ |
| Ratio[1] | 109.90% | 111.65% | 67.48% |
| 90% Geometric C.I.[2] | 102.59%- 117.74% | 104.09%- 119.75% | 60.28%- 75.54% |

[1]Calculated using geometric means according to the formula: $e^{[Formulation\ 1\ (fast)\ -\ Ritalin\ IR\ (Fast)]} \times 100$
[2]90% Geometric Confidence Interval using log-transformed data Treatment 3 (Formulation 1, Fed) Versus Treatment 4 (Ritalin®, Fed)

The ANOVAs detected statistically significant differences between treatments for ln-transformed $AUC_{0-t}$, $AUC_{0-inf}$ and $C_{max}$, and untransformed $T_{max}$, $K_{el}$, $T_{1/2\ el}$. Duncan's Multiple Range Test detected statistically significant differences between treatments 3 and 4 for all parameters with the exception of ln-transformed $AUC_{0-t}$ and $AUC_{0-inf}$. With the exception of $C_{max}$, all formulation ratios, as well as 90% geometric confidence intervals of the relative mean $AUC_{0-t}$ and $AUC_{0-inf}$ of the test product (Formulation 1) to reference product (Ritalin) were found to be within the 80% to 125%. This is summarized in Table 21 below:

TABLE 21

| Formulation 1 (Fed) vs. Ritalin ® IR (Fed) | | | |
|---|---|---|---|
| | $AUC_{0-t}$ | $AUC_{0-inf}$ | $C_{max}$ |
| Ratio[1] | 104.08% | 105.86% | 64.38% |
| 90% Geometric C.I.[2] | 97.15%- 111.50% | 98.70%- 113.55% | 57.51%- 72.07% |

[1]Calculated using geometric means according to the formula: $e^{[Formulation\ 1\ (fed)\ -\ Ritalin\ IR\ (fed)]} \times 100$
[2]90% Geometric Confidence Interval using log-transformed data Conclusions Review of individual plasma MPH time curves indicates the following:

Plasma MPH concentrations at 12 hours were higher on Formulation 1 than on Ritalin IR in all subjects, under both fed and fasted conditions.

A biphasic profile was apparent under fasted conditions in 7-10/12 subjects and in 8-10/12 under fed conditions. The mean curve showing a stable plateau under fasted conditions is therefore not fully representative of the individual profiles. The enteric coat therefore gave rise to a biphasic profile in some subjects even under fasted conditions.

Under fasted conditions the apparent rate of rise of plasma MPH was equivalent to, or faster than, that of Ritalin IR in 8/12 subjects under fasted conditions and 4-5/12 subjects under fed conditions. The mean curves which demonstrate an equivalent rate of rise under fasted conditions and a slower rise under fed conditions were therefore largely reflective of the individual profiles.

The bioavailability of Formulation 1 relative to Ritalin IR was acceptable under both fed and fasted conditions (Relative $AUC_{inf}$ 106% and 112%). There was an increase in AUC of both Formulation 1 and Ritalin when given with food (13.1% and 17.9% respectively).

Formulation 1 had a more prolonged mean plasma MPH concentration time profile than two doses of Ritalin IR. An across study comparison indicates that Formulation 1 also has a more prolonged profile than Ritalin SR.

Under fasted conditions Formulation 1 had a mean initial rate of rise of plasma MPH that is similar to Ritalin IR and a relatively flat plateau until 8 hours post-dose.

Under fed conditions, the initial rise in plasma MPH from Formulation 1 was slower than under fasted conditions and the plateau showed a biphasic profile. This was consistent with predictions that the enteric coat would delay release of the controlled release component and that this delay would be longer under fed conditions (allowing the initial plasma concentration peak, due to the IR component, to fall prior to the start of release from the controlled release component).

Formulation 1 results in both a fast initial rate of rise of plasma methylphenidate concentration, and a prolonged duration. The transformation from a prolonged plateau profile under fasted conditions to a biphasic profile under fed conditions, is as predicted. Formulation 1 therefore has the potential to meet the dual objectives of rapid onset and prolonged duration that are considered desirable characteristics of a controlled release methylphenidate formulation for the treatment of ADD/ADHD.

An initial pilot bioavailability study completed in adult healthy volunteers has confirmed that a single 20 mg dose of this formulation has an equivalent extent of absorption to two doses of immediate release methylphenidate (10 mg) given 4 hours apart. Maximal plasma concentrations with the controlled release formulation are similar to those attained with the first dose of immediate release methylphenidate and from approximately 10 hours post-dose, are higher than those following the second dose of immediate release methylphenidate.

The results indicate the potential for a single morning dose of this formulation to produce clinical effects that are at least equivalent to those of two doses of immediate-release methylphenidate given at breakfast and lunchtime, with a duration of action that may reduce the need for a third dose of immediate release methylphenidate later in the day.

EXAMPLE 8

Five-Way Comparison of Single Dose Formulation 2 (Fed and Fasted) Single Dose Formulation 3 (Fed and Fasted) and Single Dose Ritalin SR (Fasted)

A five-way blind study was conducted which compared a single dose of Formulation 2, 20 mg, both fed and fasted, a single dose of Formulation 3, 20 mg, both fed and fasted, and Ritalin SR 20 mg single dose fasted. According to the published literature and anecdotal comments from physicians, Ritalin SR is used in less than 20% of methylphenidate treated patients.

Twelve healthy male volunteers were given a single dose of either 20 mg Formulation 2 or Formulation 3 administered four hours apart under both fed and fasting conditions (n=2), or slow-release 20 mg methylphenidate (Ritalin SR) under fasting conditions. "Fed" conditions indicates the test formulation was given to the subjects after they had eaten a high-fat breakfast. Following an overnight fast of at least 10.0 hours, each of the normal, healthy, non-smoking, male subjects were given the following treatments according to Williams design 5 treatment randomization scheme.

Treatment 1: Test Product: methylphenidate controlled-release, Formulation 2, 20 mg capsule, in the morning under fasting conditions.

Treatment 2: Test Product: methylphenidate controlled-release, Formulation 2, 20 mg capsule, in the morning, under fed conditions.

Treatment 3: Test Product: methylphenidate controlled-release, Formulation 3, 20 mg capsule, under fasting conditions.

Treatment 4: Test Product: methylphenidate controlled-release, Formulation 3, 20 mg capsule, under fed conditions.

Treatment 5: Reference Product: methylphenidate slow-release 20 mg tablet Ritalin SR (Novartis) under fasting conditions.

There was a seven day washout period between the study periods. During each study period, blood samples (1×5 mL each) were taken from each subject within one hour prior to dosing and at 0.250, 0.500, 0.750, 1.00, 1.50, 2.00, 2.50, 3.00, 3.50, 4.00, 4.50, 5.00, 6.00, 7.00, 8.00, 10.0, 12.0, 16.0, 24.0 hours post-dose. Plasma was harvested from each blood sample and stored in a −20 C freezer until assayed for plasma methylphenidate concentration.

Figure 5:
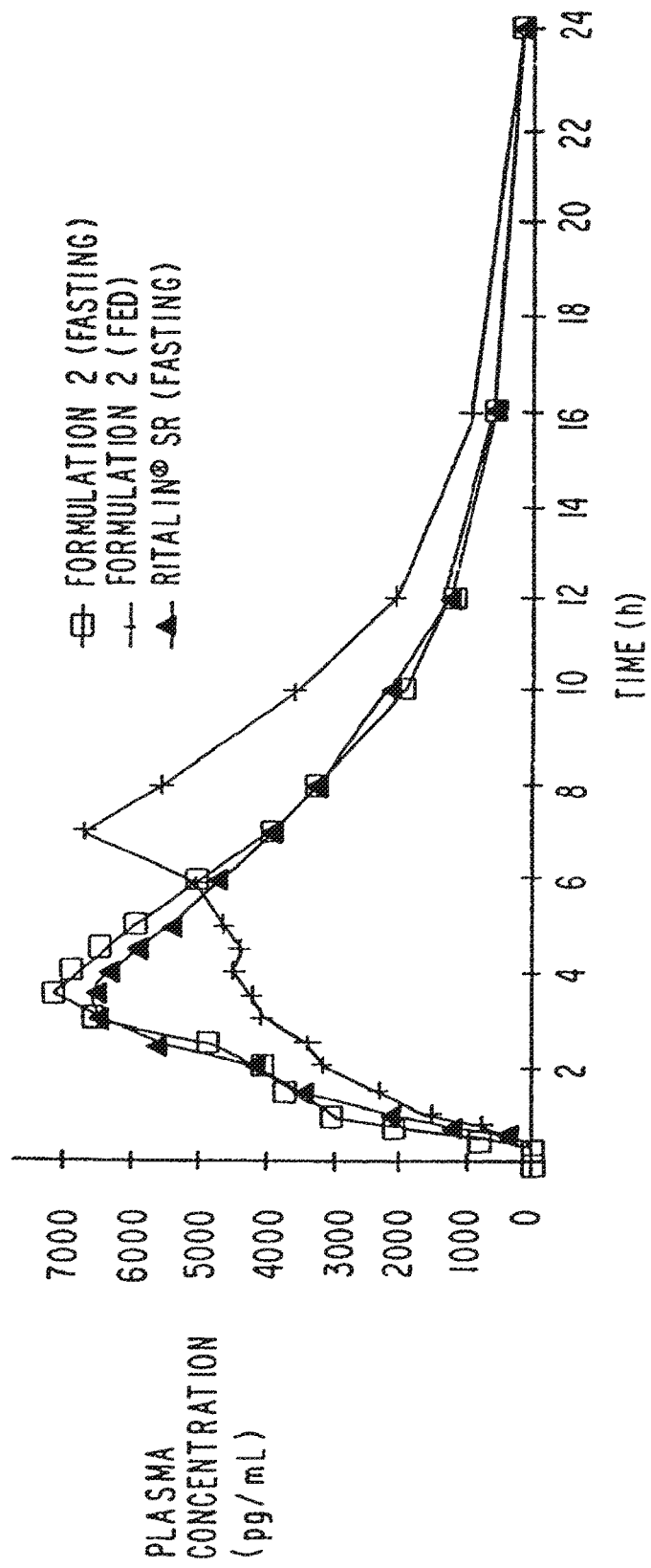
FIG. 5 is a graphical comparison of the mean plasma concentration of methylphenidate when test subjects are treated with Formulation 2 under fasting and fed conditions, and Ritalin® SR under fasting conditions, as a function of time.
Figure 6:
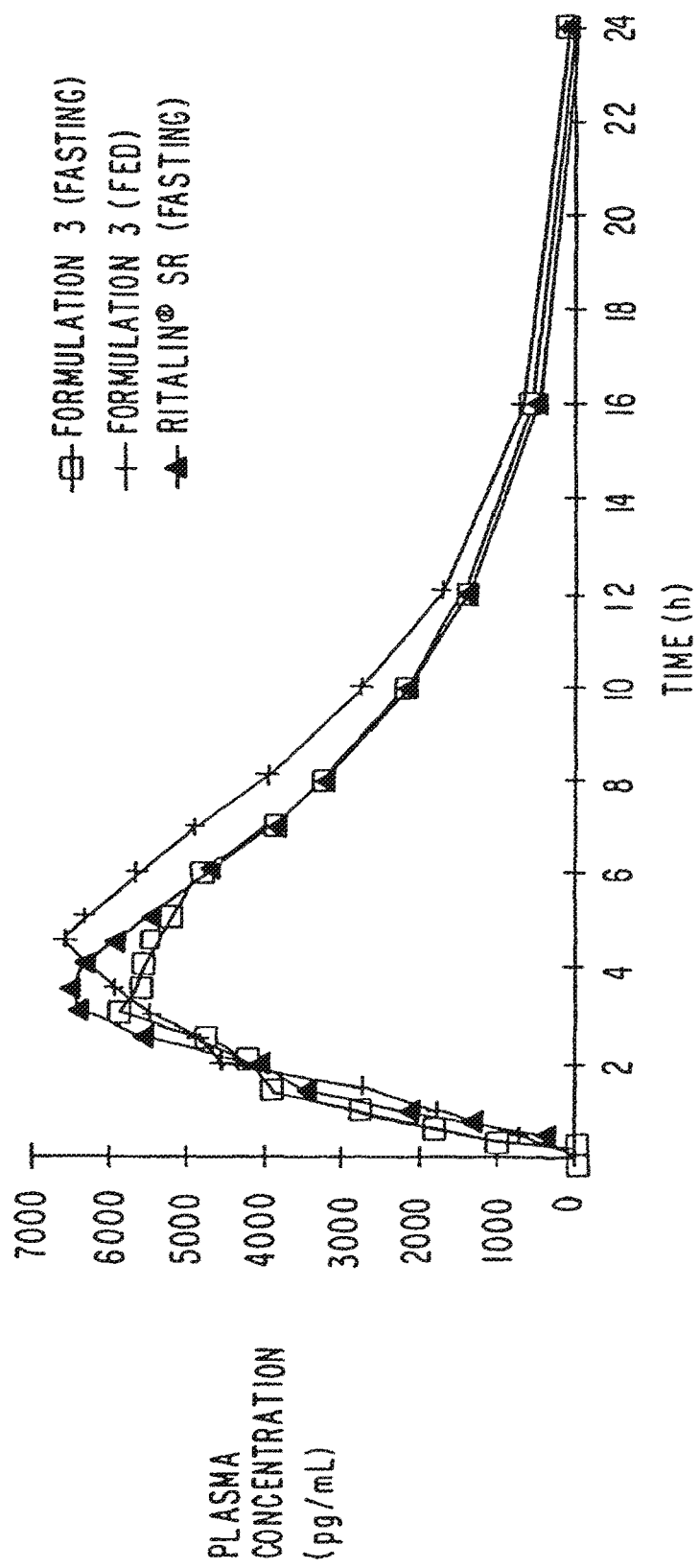
FIG. 6 is a graphical comparison of the mean plasma concentration of methylphenidate when test subjects are treated with Formulation 3 under fasting and fed conditions, and Ritalin® SR under fasting conditions, as a function of time.
Figure 7:
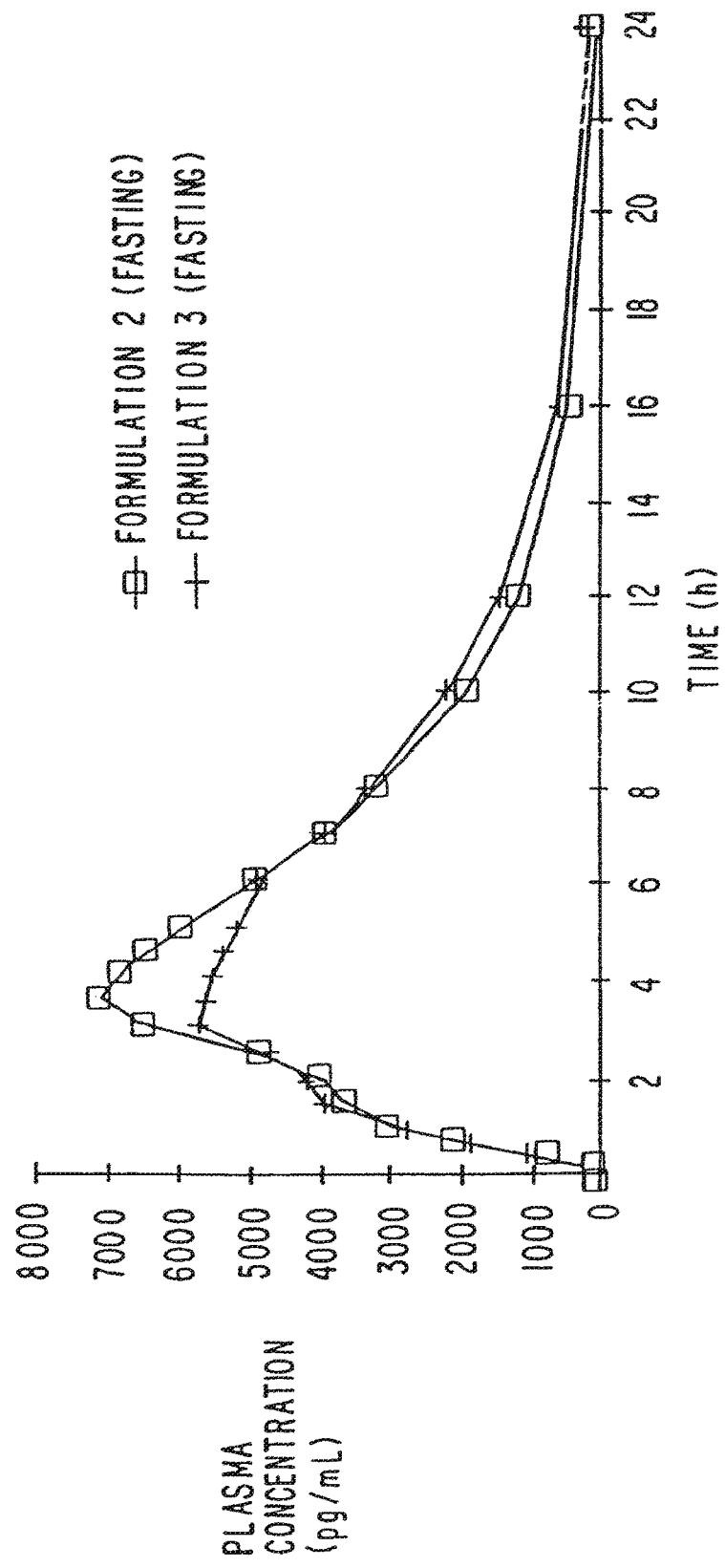
FIG. 7 is a graphical comparison of the mean plasma concentration of methylphenidate when test subjects are treated with Formulations 2 and 3 under fasting conditions as a function of time.
Figure 8:
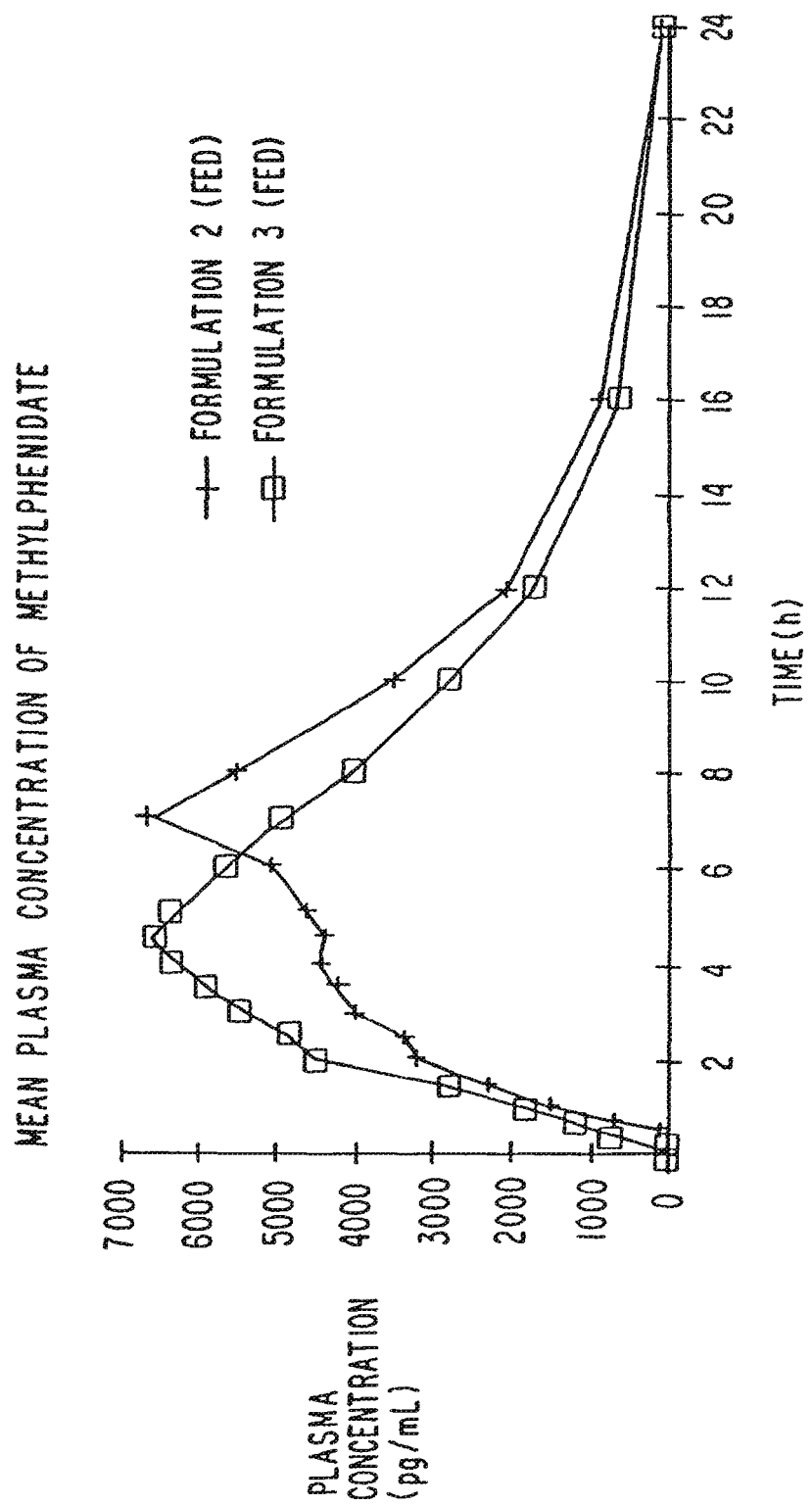
FIG. 8 is a graphical comparison of the mean plasma concentration of methylphenidate when test subjects are treated with Formulations 2 and 3 under fed conditions as a function of time.

The data is presented graphically in FIGS. 5-8. FIG. 5 presents the mean plasma concentration versus time for Formulation 2 under fasting and fed conditions and Ritalin® under fasting conditions. FIG. 6 presents the mean plasma concentration versus time for Formulation 3 under fasting and fed conditions and Ritalin® under fasting conditions. FIG. 7 presents the mean plasma concentration versus time for Formulations 2 and 3 under fasting conditions. FIG. 8 presents the mean plasma concentration versus time for Formulations 2 and 3 under fed conditions.

The complete pharmacokinetic parameters of controlled release methylphenidate 20 mg (Formulation 2 and 3) under fed and fasting conditions, and for slow release methylphenidate 20 mg (Ritalin® SR) under fasting conditions are summarized in Tables 22-24 below.

TABLE 22

Pharmacokinetic Parameters for Formulation 2

| Parameters | | Treatment 1, Fasting | | Treatment 2, Fed | |
|---|---|---|---|---|---|
| | | Means ± SD | CV(%) | Mean ± SD | CV(%) |
| $AUC_{0-t}$ | (pg · h/mL) | 48190.73 ± 11668.71 | 24.21 | 53452.63 ± 12820.39 | 23.98 |
| $AUC_{0-inf}$ | (pg · h/mL) | 49787.07 ± 12053.23 | 24.21 | 55690.49 ± 12691.52 | 22.79 |
| $C_{max}$ | (pg · h/mL) | 7498.57 ± 1968.38 | 26.25 | 6879.09 ± 1486.53 | 21.63 |
| $T_{max}$ | (h) | 3.63 ± 0.57 | 15.70 | 6.42 ± 1.08 | 16.89 |
| $K_{el}$ | (h$^{-1}$) | 0.2391 ± 0.0428 | 17.91 | 0.2323 ± 0.0342 | 14.75 |
| $T_{1/2}$ | (h) | 3.00 ± 0.64 | 21.32 | 3.05 ± 0.48 | 15.74 |

TABLE 23

Pharmacokinetic Parameters for Formulation 3

| Parameters | | Treatment 3, Fasting | | Treatment 4, Fed | |
|---|---|---|---|---|---|
| | | Means ± SD | CV(%) | Mean ± SD | CV(%) |
| $AUC_{0-t}$ | (pg · h/mL) | 48057.06 ± 14743.87 | 30.68 | 54128.75 ± 14787.94 | 27.32 |
| $AUC_{0-inf}$ | (pg · h/mL) | 49984.68 ± 14873.03 | 29.76 | 56315.66 ± 34779.59 | 26.24 |
| $C_{max}$ | (pg · h/mL) | 6080.97 ± 2048.60 | 33.69 | 6959.07 ± 1559.34 | 22.41 |
| $T_{max}$ | (h) | 3.46 ± 0.89 | 25.76 | 4.42 ± 0.56 | 12.62 |
| $K_{el}$ | (h$^{-1}$) | 0.2009 ± 0.0468 | 23.32 | 0.2057 ± 0.0390 | 18.97 |
| $T_{1/2}$ | (h) | 3.65 ± 0.97 | 26.52 | 3.49 ± 0.70 | 20.01 |

TABLE 24

Pharmacokinetic Parameters for Ritalin SR ®

| Parameters | Mean ± SD | CV (%) |
|---|---|---|
| $AUC_{0-t}$ (pg · h/mL) | 47404.51 ± 12754.66 | 26.91 |
| $AUC_{0-inf}$ (pg · h/mL) | 49252.17 ± 12841.52 | 26.07 |
| $C_{max}$ (pg · h/mL) | 6783.09 ± 1496.65 | 22.06 |
| $T_{max}$ (h) | 3.50 ± 0.43 | 12.18 |
| $K_{el}$ (h$^{-1}$) | 0.2282 ± 0.0320 | 14.01 |
| $T_{1/2}$ (h) | 3.10 ± 0.47 | 15.14 |

The results of the ANOVA and Duncan's Multiple Range Test performed on the ln-transformed $C_{max}$ data show a statistically significant difference between treatments for this parameter. According to Duncan's Multiple Range Test, the $C_{max}$ of treatment 3 was significantly different from the $C_{max}$ of treatments 4 and 5. However, Duncan's Multiple Range Test did not detect statistically significant differences between treatments for $C_{max}$ when comparing treatment 1 vs. treatment 2 or treatment 1 vs treatment 5. The statistical analyses performed on the data are summarized in Table 25 below:

TABLE 25

| $C_{max}$ (pg/mL) | TRT 1 vs. TRT 2 | TRT 3 vs. TRT 4 | TRT 1 vs. TRT 5 | TRT 3 vs. TRT 5 |
|---|---|---|---|---|
| Ratio | 103.73% | 84.78% | 109.25% | 87.40% |
| 90% Geometric C.I. | 98.94% to 115.14% | 78.59% to 91.45% | 101.28% to 117.85% | 81.05% to 94.26% |

The ANOVA and Duncan's Multiple Range Test performed on the ln-transformed $T_{max}$ data detected a statistically significant difference between treatments for this parameter. Duncan's Multiple Range Test detected statistically significant differences between treatments 1 and 2, and treatments 3 and 4 for this parameter. Duncan's Multiple Range Test did not detect statistically significant differences between treatments for $T_{max}$ when comparing treatments 1 vs. 3 or treatments 3 vs. 5.

The ANOVA performed on the $T_{1/2\ el}$ data detected a statistically significant difference between treatments for this parameter. Duncan's Multiple Range Test detected no statistically significant differences between treatments 1 and 2, treatments 3 and 4, and treatments 1 and 5 for $T_{1/2\ el}$. However, Duncan's Multiple Range Test detected statistically significant differences between treatments 3 and 5 for this parameter.

The ANOVA performed on the $K_{el}$ data show a statistically significant difference between treatments for this parameter. Statistically significant differences were not detected by Duncan's Multiple Range Test, between treatments for $K_{el}$ when comparing treatments 1 and 2, treatments 3 and 4, or treatments 1 and 5. However, Duncan's Multiple Range Test detected statistically significant differences between treatments 3 and 5 for this parameter.

The ANOVA and Duncan's Multiple Range Test performed on the ln-transformed $AUC_{0-t}$ data show a statistically significant difference between treatments for this parameter. According to Duncan's Multiple Range Test, the $AUC_{0-t}$ of treatments 1 and 3 was significantly different from the $AUC_{0-t}$ of treatments 2 and 4 respectively. However, Duncan's Multiple Range Test did not detect statistically significant differences between treatments for $AUC_{0-t}$ when comparing treatment 1 vs treatment 5, or treatment 3 vs treatment 5. The statistical analyses performed on the data are summarized below in Table 26:

TABLE 26

| $AUC_{0-t}$ (pg · h/mL) | Treatment 1 vs. Treatment 2 | Treatment 3 vs. Treatment 4 | Treatment 1 vs. Treatment 5 | Treatment 3 vs. Treatment 5 |
|---|---|---|---|---|
| Ratio | 89.21% | 88.23% | 101.82% | 100.63% |
| 90% Geometric C.I. | 84.03% to 94.71% | 83.10% to 93.67% | 95.91% to 108.10% | 94.81% to 106.81% |

The ANOVA and Duncan's Multiple Range Test performed on the ln-transformed $AUC_{0-inf}$ data show a statistically significant difference between treatments for this parameter. According to Duncan's Multiple Range Test, the $AUC_{0-inf}$ of treatments 1 and 3 was significantly different from the $AUC_{0-inf}$ of treatments 2 and 4 respectively. However, Duncan's Multiple Range Test did not detect statistically significant differences between treatments for $AUC_{0-inf}$ when comparing treatment 1 vs treatment 3, or treatment 3 vs treatment 5. The statistical analyses performed on the data are summarized below in Table 27:

TABLE 27

| $AUC_{0-inf}$ (pg · h/mL) | TRT 1 vs. TRT 2 | TRT 3 vs. TRT 4 | TRT 1 vs. TRT 5 | TRT 3 vs. TRT 5 |
|---|---|---|---|---|
| Ratio | 88.33% | 88.14% | 101.14% | 100.82% |
| 90% Geometric C.I. | 83.50% to 93.44% | 83.32% to 93.24% | 95.61% to 106.99% | 95.33% to 106.63% |

Treatment 1 (Formulation 2, Fasting) Vs. Treatment 2 (Formulation 2, Fed)

The ANOVAs detected statistically significant differences between fed and fasting conditions, treatments 1 and 2, for the ln-transformed $AUC_{0-t}$, $AUC_{0-inf}$ and $C_{max}$ and untransformed $T_{max}$, $T_{1/2el}$ and $K_{el}$. Duncan's Multiple Range Test detected statistically significant differences between treatments 1 and 2 for ln-transformed $AUC_{0-t}$ and $AUC_{0-inf}$ and untransformed $T_{max}$. However, Duncan's Multiple Range Test detected no statistically significant differences between treatments for ln-transformed $C_{max}$ and untransformed $T_{1/2el}$ and $K_{el}$. All formulation ratios, as well as 90% geometric confidence intervals of the relative mean $AUC_{0-t}$, $AUC_{0-inf}$ and $C_{max}$ were found to be within the 80% to 125%, as is shown in Table 28 below. Thus, it appears that food increases the extent of absorption of methylphenidate for Formulation 2. However, this food effect was less than 20% on average.

TABLE 28

Formulation 2, Fed versus Fasting

| | $AUC_{0-t}$ | $AUC_{0-inf}$ | $C_{max}$ |
|---|---|---|---|
| Ratio[1] | 112.09% | 113.21% | 93.69% |
| 90% Geometric C.I.[2] | 105.58% to 119.00% | 107.03% to 119.76% | 86.85% to 101.07% |

[1]Calculated using geometric means according to the formula: $e^{(Formulation\ 2(Fed) - Formulation\ 2\ (Fasting))} \times 100$
[2]90% Geometric Confidence Interval using ln-transformed data Treatment 3 (Formulation 3, Fasting) Vs. Treatment 4 (Formulation 3, Fed)

The ANOVAs detected statistically significant differences between treatments for ln-transformed $AUC_{0-t}$, $AUC_{0-inf}$ and $C_{max}$ and untransformed $T_{max}$, $T_{1/2el}$ and $K_{el}$. Duncan's Multiple Range Test detected statistically significant differences between treatments 3 and 4 for ln-transformed $AUC_{0-t}$, $AUC_{0-inf}$ and $C_{max}$ and untransformed $T_{max}$. However, Duncan's Multiple Range Test detected no statistically significant differences between treatments for untransformed $T_{1/2el}$ and $K_{el}$. With the exception of lower 90% geometric confidence interval for $C_{max}$, all formulation ratios, as well as 90% geometric confidence intervals of the relative mean $AUC_{0-t}$, $AUC_{0-inf}$ and $C_{max}$ were found to be within the 80% to 125%, as is shown in Table 29 below. Thus, it appears that food increases the extent of absorption of methylphenidate for Formulation 3. However, this food effect was less than 20% on average.

TABLE 29

Formulation 3, Fed versus Fasting

| | $AUC_{0-t}$ | $AUC_{0-inf}$ | $C_{max}$ |
|---|---|---|---|
| Ratio[1] | 113.35% | 113.45% | 117.96% |
| 90% Geometric C.I.[2] | 106.76% to 120.33% | 107.25% to 120.01% | 109.35% to 127.25% |

[1]Calculated using geometric means according to the formula: $e^{(Formulation\ 3\ (fed) - Formulation\ 3\ (Fasting))} \times 100$
[2]90% Geometric Confidence Interval using ln-transformed data Treatment 1 (Formulation 2, Fasting) Vs. Treatment 5 (Ritalin SR®, Fasting)

The ANOVAs detected statistically significant differences between treatments for ln-transformed $AUC_{0-t}$, $AUC_{0-inf}$ and $C_{max}$ and untransformed $T_{max}$, $T_{1/2el}$ and $K_{el}$. Duncan's Multiple Range Test detected no statistically significant differences between treatments 1 and 5 for all parameters. All formulation ratios, as well as 90% geometric confidence intervals of the relative mean $AUC_{0-t}$, $AUC_{0-inf}$ and $C_{max}$ of the test to reference product were found to be within the 80% to 125%, as shown in Table 30 below. Thus, Formulation 2 is bioequivalent to the reference product Ritalin SR® under fasting conditions.

TABLE 30

Formulation 2 (Fasting) versus Ritalin SR (Fasting)

| | $AUC_{0-t}$ | $AUC_{0-inf}$ | $C_{max}$ |
|---|---|---|---|
| Ratio[1] | 101.82% | 101.14% | 106.99% |
| 90% Geometric C.I.[2] | 95.91% to 108.10% | 95.61% to 106.99% | 101.28 to 117.85% |

[1]Calculated using geometric means according to the formula: $e^{(Formulation\ 2\ (fast) - Ritalin\ SR\ (Fast))} \times 100$
[2]90% Geometric Confidence Interval using ln-transformed data Treatment 3 (Formulation 3, Fasting) Vs. Treatment 5 (Ritalin SR®, Fasting)

The ANOVAs detected statistically significant differences between treatments for ln-transformed $AUC_{0-t}$, $AUC_{0-inf}$ and $C_{max}$ and untransformed $T_{max}$, $T_{1/2el}$ and $K_{el}$. Duncan's Multiple Range Test detected statistically significant differences between treatments 3 and 5 for ln-transformed $C_{max}$ and untransformed $T_{1/2el}$ and $K_{el}$. However, Duncan's Multiple Range Test detected no statistically significant differences between treatments for ln-transformed $AUC_{0-t}$ and $AUC_{0-inf}$ and untransformed $T_{max}$. All formulation ratios, as well as 90% geometric confidence intervals of the relative mean $AUC_{0-t}$, $AUC_{0-inf}$ and $C_{max}$ of the test to reference product were found to be within the 80% to 125%, as shown in Table 31 below. Thus, Formulation 3 is bioequivalent to the reference product Ritalin SR® under fasting conditions.

TABLE 31

Formulation 3 (Fasting) versus Ritalin SR (Fasting)

|  | $AUC_{0-t}$ | $AUC_{0-inf}$ | $C_{max}$ |
|---|---|---|---|
| Ratio[1] | 101.63% | 100.82% | 87.40% |
| 90% Geometric C.I.[2] | 94.81% to 106.81% | 95.33% to 106.63% | 81.05 to 94.26% |

[1] Calculated using geometric means according to the formula: $e^{(Formulation\ (fast) - Ritalin\ SR\ (Fast))} \times 100$
[2] 90% Geometric Confidence Interval using ln-transformed data Conclusions The bioavailability of Formulation 2 relative to Ritalin SR® is acceptable under fasted conditions (Relative $AUC_{inf}$ 101%—Fed conditions not tested) The bioavailability of Ritalin SR® under fasted conditions is similar to that of Ritalin® IR, as discussed in Example 7 ($AUC_{inf}$ 29.2 vs. 46.5 ng·h/mL, respectively). Literature data which indicates that Ritalin® IR and SR are absorbed at equivalent rates suggests that comparisons between the studies presented in Examples 7 and 8 are reasonable.

Bioavailability of Formulations 1 and 2 are similar under fasted and fed conditions (fasted: 49.8 vs. 51.2 ng·h/mL; fed: 55.7 vs. 57.9 ng·h/mL).

From the mean curves of Formulation 2 and Ritalin SR®, the initial rate of rise of plasma MPH concentration is slightly faster for Formulation 2 compared to Ritalin SR®. Under fed conditions, the rate of rise of plasma MPH with Formulation 2 decreased and $T_{max}$ was delayed in comparison to both Formulation 2 fasted and Ritalin SR® fasted.

Bioavailability of Formulation 3 relative to Ritalin SR® is acceptable under fasted conditions (Relative $AUC_{inf}$ 100.8%—fed conditions not tested).

Bioavailability of Formulations 1 and 3 are similar under fasted and fed conditions (fasted: 50.0 versus 51.2 ng/hmL; fed: 56.3 versus 57.9 ng·h/mL). Note also that Formulations 2 and 3 have almost identical AUC values.

From the mean curves of Formulation 3 and Ritalin SR®, the initial rate of rise of plasma MPH concentrations is slightly faster for Formulation 3 compared to Ritalin SR®.

In contrast to Formulation 2, the effect of food on the initial rate of concentration rise is minimal. Since Formulation 3 does not contain an enteric coat, this suggests that food slows the initial release from the IR component of formulations that contain an enteric coat, both when the enteric coat is part of the same bead (underneath the IR coat in the case of Formulation 1) and when it is in a separate bead (as for Formulation 2).

Also in contrast to Formulation 2, the $T_{max}$ of the mean curve of Formulation 3 occurs at a similar time to that of Ritalin SR® under fed and fasted conditions. For Formulation 2 (and Formulation 1) the $T_{max}$ of the second absorption phase under fed conditions is substantially delayed relative to Ritalin SR®.

Conclusions—Examples 7 and 8

1. Formulation 1 has both a fast initial rate of rise, at least under fasted conditions and a prolonged duration. The transformation from a prolonged plateau profile under fasted conditions to a biphasic profile under fed conditions, is as predicted. Since these conditions represent the extremes of "food stress", one might predict that administration in association with normal meals and times would provide an intermediate profile. It is also possible that gastric emptying in children on a normal meal schedule will be faster than in adults fed a high fat meal—this will tend to make the second absorption phase occur earlier and produce lower concentrations from 12 hours onwards. Formulation 1 therefore meets the dual objectives of rapid onset and prolonged duration.

2. Formulation 2 is also very similar to Ritalin SR® under fasted conditions but shows a delayed peak under fed conditions such that plasma MPH concentrations are higher than Ritalin SR® (fasted) from 6 hours post dose onwards. The controlled release component in Formulation 2 is faster releasing than the one in Formulation 1 and plasma MPH concentrations are lower for Formulation 2 from about 10 hours post dose.

3. Overall, Formulation 3 (non-enteric coated) has a profile very similar to Ritalin SR® under both fed and fasted conditions. The IR component of Formulation 3 provides some increase in initial absorption rate relative to Ritalin SR® under fasted conditions. Since concentrations later in the day are similar for the two formulations, this confirms the concept that a fast initial rise and higher concentrations later in the day are not possible at the same dose, unless a delay is introduced into the release of a component of the total dose.

The examples provided above are not meant to be exclusive. Many other variations of the present invention would be obvious to those skilled in the art, and are contemplated to be within the scope of the appended claims.

What is claimed is:

1. An oral controlled release formulation, comprising
    a plurality of substrates in the form of matrix spheroids or inert pharmaceutically acceptable beads, wherein said plurality of substrates comprise a portion of an effective dose of methylphenidate or a pharmaceutically acceptable salt thereof in immediate release form incorporated into the matrix spheroids or coated over the inert pharmaceutically acceptable beads,
    a hydrophobic material comprising an acrylic polymer coated onto the surface of said substrates in an amount sufficient to retard the release of said portion of the methylphenidate or pharmaceutically acceptable salt thereof, and
    an enteric coating applied over said hydrophobic material to obtain enteric coated substrates, wherein said enteric coating is in an amount sufficient to substantially delay the release of said methylphenidate or pharmaceutically acceptable salt thereof from said substrates until after said formulation passes through the stomach, wherein said enteric coating is derived from an aqueous dispersion comprising an acrylic/methacrylic copolymer, a plasticizer and a glidant,
    the formulation further comprising the remaining portion of the effective dose of the methylphenidate or pharmaceutically acceptable salt thereof in immediate release form, and
    wherein the formulation provides a maximum plasma concentration of methylphenidate at about 0.5 to about 2 hours after oral administration,
    and the duration of effect provided by the methylphenidate or pharmaceutically acceptable salt thereof contained in the formulation falls below effective plasma concentrations at about 10 to about 12 hours after the oral administration.

2. The oral controlled release formulation of claim 1, wherein said formulation comprises methylphenidate hydrochloride.

3. The oral controlled release formulation of claim 2, wherein said remaining portion of the effective dose of methylphenidate hydrochloride is applied as a topcoat over the enteric coated substrates.

4. The oral controlled release formulation of claim 3, wherein said topcoat of methylphenidate hydrochloride is obtained through spraying a solution of methylphenidate hydrochloride in water over the enteric coated substrates.

5. The oral controlled release formulation of claim 2, wherein the enteric coated substrates are contained within a capsule.

6. The oral controlled release formulation of claim 5, wherein the capsule is coated with the remaining portion the effective dose of methylphenidate hydrochloride in the immediate release form.

7. The oral controlled release formulation of claim 5, wherein said remaining portion of methylphenidate hydrochloride is incorporated into the capsule in the form of an immediate release powder within the capsule.

8. The oral controlled release formulation of claim 5, wherein said remaining portion of the effective dose of methylphenidate hydrochloride is incorporated into the capsule in the form of an immediate release granulate within the capsule.

9. The oral controlled release formulation of claim 2, wherein the enteric coated substrates are contained within a tablet.

10. The oral controlled release formulation of claim 9, wherein the tablet is coated with the remaining portion of the effective dose of methylphenidate hydrochloride in the immediate release form.

11. The oral controlled release formulation of claim 2, wherein said remaining portion of the effective dose of methylphenidate hydrochloride is incorporated into the formulation in the form of immediate release substrates, wherein the enteric coated substrates are mixed with the immediate release substrates within the oral controlled release formulation.

12. The oral controlled release formulation of claim 11, wherein said immediate release substrates are obtained through spraying an aqueous solution comprising methylphenidate hydrochloride onto a second plurality of substrates.

13. The oral controlled release formulation of claim 11, wherein the immediate release substrates are selected from the group of immediate release beads, immediate release ion exchange resins, immediate release pellets, immediate release spheroids, and immediate release spheres.

14. The oral controlled release formulation of claim 2, wherein the maximum plasma concentration occurs at about 0.5 to about 1 hour after the oral administration.

15. The oral controlled release formulation of claim 14, wherein the maximum plasma concentration occurs at about 1 hour after the oral administration.

16. The oral controlled release formulation of claim 15, wherein the maximum plasma concentration occurs under fasting conditions.

17. The oral controlled release formulation of claim 2, wherein the maximum plasma concentration occurs at about 1 to about 2 hours after the oral administration.

18. The oral controlled release formulation of claim 2, wherein the remaining portion of the effective dose contains from about 30% to about 40% of the effective dose of the methylphenidate or pharmaceutically acceptable salt thereof.

19. The oral controlled release formulation of claim 2, wherein the duration of effect provided by the methylphenidate or pharmaceutically acceptable salt thereof contained in the formulation falls below effective plasma concentrations at about 12 hours after the oral administration.

20. The oral controlled release formulation of claim 19, wherein the remaining portion of the effective dose contains from about 30% to about 40% of the effective dose of the methylphenidate or pharmaceutically acceptable salt thereof.

21. An oral controlled release formulation, comprising
a plurality of substrates in the form of matrix spheroids or inert pharmaceutically acceptable beads, wherein said plurality of substrates comprise a portion of an effective dose of methylphenidate or a pharmaceutically acceptable salt thereof incorporated into the matrix spheroids or coated over the inert pharmaceutically acceptable beads,
a controlled release coating comprising an acrylic polymer coated onto the surface of said substrates, and
an enteric coating applied over said controlled release coating to obtain enteric coated substrates, wherein said enteric coating is derived from an aqueous dispersion comprising an acrylic/methacrylic copolymer, a plasticizer and a glidant, and is in an amount sufficient to delay the release of said portion of the effective dose of the methylphenidate or pharmaceutically acceptable salt thereof from said enteric coated substrates until after said formulation passes through the stomach,
the formulation further comprising the remaining portion of the effective dose in an immediate release form, and
providing a time to maximum plasma concentration of methylphenidate at about 0.5 to about 2 hours after oral administration, and a duration of effect for a time period of from about 10 to about 12 hours.

22. The oral controlled release formulation of claim 21, wherein said formulation comprises methylphenidate hydrochloride.

23. The oral controlled release formulation of claim 22, wherein said remaining portion of the effective dose is applied as a topcoat over the enteric coated substrates.

24. The oral controlled release formulation of claim 22, wherein the enteric coated substrates are contained within a capsule.

25. The oral controlled release formulation of claim 22, wherein the enteric coated substrates are contained within a tablet.

26. The oral controlled release formulation of claim 22, wherein said remaining portion of the effective dose is incorporated into the formulation in the form of immediate release substrates, and the oral controlled release formulation comprises a mixture of the enteric coated substrates and the immediate release substrates.

27. The oral controlled release formulation of claim 21, wherein the oral administration is under fasting conditions.

28. The oral controlled release formulation of claim 21, wherein said remaining portion of the effective dose comprises from about 30% to about 40% of the effective dose.

29. The oral controlled release formulation of claim 21, wherein the portion of the effective dose is coated over said inert pharmaceutically acceptable beads, and the plasticizer comprises from about 1 to about 50 percent of the acrylic/methacrylic acid copolymer by weight.

30. The oral controlled release formulation of claim 1, wherein the portion of the effective dose is coated over said inert pharmaceutically acceptable beads, and the plasticizer comprises from about 1 to about 50 percent of the acrylic/methacrylic acid copolymer by weight.

31. An oral controlled release formulation, comprising a plurality of substrates in the form of inert pharmaceutically acceptable beads, comprising a portion of an effective dose of methylphenidate or a pharmaceutically acceptable salt thereof coated over said inert pharmaceutically acceptable beads, a controlled release coating comprising an acrylic polymer coated onto the surface of said substrates, and an enteric coating applied over said controlled release coating to obtain enteric coated substrates, wherein said enteric coating is derived from an aqueous dispersion comprising an acrylic/methacrylic copolymer, a plasticizer and a glidant, and is in an amount sufficient to delay the release of said portion of the effective dose of the methylphenidate or pharmaceutically acceptable salt thereof from said enteric coated substrates until after said formulation passes through the stomach, the formulation further comprising the remaining portion of the effective dose in an immediate release form, wherein the acrylic polymer is a copolymer of acrylic and methacrylic esters having a molar ratio of ammonium groups to the remaining neutral (meth)acrylic esters of 1:40, the acrylic/methacrylic acid copolymer is a methacrylic acid copolymer which does not swell at about pH<5.7 and is soluble at about pH>6, and the plasticizer comprises from about 1 to about 50 percent of the methacrylic acid copolymer by weight.

32. An oral controlled release formulation, comprising a plurality of substrates comprising a portion of an effective dose of methylphenidate or a pharmaceutically acceptable salt thereof is coated over inert pharmaceutically acceptable beads, a controlled release coating comprising an acrylic polymer coated onto the surface of said substrates, and an enteric coating applied over said controlled release coating to obtain enteric coated substrates, wherein said enteric coating is derived from an aqueous dispersion comprising an acrylic/methacrylic copolymer, a plasticizer and a glidant, and is in an amount sufficient to delay the release of said portion of the effective dose of the methylphenidate or pharmaceutically acceptable salt thereof from said enteric coated substrates until after said formulation passes through the stomach, the formulation further comprising the remaining portion of the effective dose in an immediate release form, wherein the formulation provides a mean $AUC_{0-t}$ of 54686.38+15118.66 pg×h/ml, a mean $AUC_{0-inf}$ of 57931.47+16762.54 pg×h/ml, a mean $C_{max}$ of 4879.37 +1027.85 pg/ml, a mean $T_{max}$ of 7.29+1.29 hours, a mean $K_{el}$ of 0.1812+0.0392h⁻, and a mean $T_{1/2el}$ of 4.06 +1.25 hours, based on a fed administration of a formulation comprising 20 mg of said methylphenidate or pharmaceutically acceptable salt thereof.

\* \* \* \* \*